(12) United States Patent
Horwell et al.

(10) Patent No.: US 6,225,352 B1
(45) Date of Patent: May 1, 2001

(54) LOW MOLECULAR WEIGHT DENDRITIC COMPOUNDS AS PHARMACEUTICAL AGENTS

(75) Inventors: David Christopher Horwell, Cambridge; Giles Stuart Ratcliffe, Hertfordshire, both of (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/230,988
(22) PCT Filed: Aug. 12, 1997
(86) PCT No.: PCT/US97/11556
  § 371 Date: Feb. 4, 1999
  § 102(e) Date: Feb. 4, 1999
(87) PCT Pub. No.: WO98/06691
  PCT Pub. Date: Feb. 19, 1998

Related U.S. Application Data

(60) Provisional application No. 60/023,693, filed on Aug. 14, 1996, and provisional application No. 60/055,101, filed on Aug. 6, 1997.

(51) Int. Cl.$^7$ .................... A61K 31/166; C07C 235/66
(52) U.S. Cl. .................. 514/617; 564/180; 548/491; 514/415; 514/622
(58) Field of Search .................. 514/415, 617, 514/622; 548/491; 564/180

(56) References Cited

U.S. PATENT DOCUMENTS

| | | | |
|---|---|---|---|
| 4,204,000 | 5/1980 | Diamond et al. | 424/304 |
| 4,241,087 | 12/1980 | Mir et al. | 424/324 |
| 5,478,924 | 12/1995 | Cramer et al. | 530/416 |
| 5,488,126 | 1/1996 | Subramanian et al. | 558/17 |
| 5,527,524 | 6/1996 | Tomalia et al. | 424/1.33 |
| 5,593,660 | 1/1997 | Krause et al. | 424/9.451 |
| 5,759,518 | 6/1998 | Schmitt-Willich et al. | 424/9.36 |

FOREIGN PATENT DOCUMENTS

| | | |
|---|---|---|
| 0341961 | 11/1989 | (EP) . |
| 0684044 | 11/1995 | (EP) . |
| 7267879 | 10/1995 | (JP) . |
| 9527902 | 10/1995 | (WO) . |
| 9528641 | 10/1995 | (WO) . |
| 9528966 | 11/1995 | (WO) . |
| 9534595 | 12/1995 | (WO) . |
| 9622321 | 7/1996 | (WO) . |

OTHER PUBLICATIONS

Issberner et al., "Dendrimers: From Generations and Functional Groups to Functions", *Angew. Chem. Int. Ed. Engl.*, vol. 33, No. 23/24, 1994, 2413–2420.

Lehn, "Perspectives in supramolecular chemistry: From molecular recognition towards self–organisation", *Pure & Appl. Chem.*, vol. 66, Nos. 10/11, 1994, 1961–1966.

Belle et al., "A Versatile Key Synthon for the Syntheses of Ligands Potentially Suited for the Preparation of $\mu$–Phenoxo Dimetallic Complexes with Two Non Equivalent Complexation Sites", *Tetrahedron Letters*, vol. 35, No. 38, 1994, 7019–7022.

Chung et al., "Synthesis and Bioactivities of Heterocyclic Lipids as PAF Antagonists. 1", *Bioorganic & Medicinal Chemistry Letters*, vol. 5, No. 10, 1995, 1091–1096.

Ojima et al., "Antithrombotic Agents: From RGD to Peptide Mimetics", *Bioorganic & Medicinal Chemistry*, vol. 3, No. 4, 1995, 337–360.

Nadasdi et al., "Structure–Activity Analysis of a Conus Peptide Blocker of N–Type Neuronal Calcium Channels", *Biochemistry*, vol. 34, 1995, 8076–8081.

Qualmann et al., "Synthesis of Boron–Rich Lysine Dendrimers as Protein Labels in Electron Microscopy", *Angew. Chem. Int. Ed. Engl.*, vol. 35, No. 8, 1996, 909–911.

Haddleton et al., "Synthesis of polyester dendrimers", *J. Chem. Soc., Perkin. Trans.* 1, 1996, 649–656.

Ferguson et al., "Calixarene–bound dendritic macromolecules", *J. Chem. Soc., Perkin Trans.* 1, 1996, 599–602.

Zeng and Zimmerman, "Rapid Synthesis of Dendrimers by an Orthogonal Coupling Strategy", *J. Am. Chem. Soc.*, vol. 118, 1996, 5326–5327.

Roy et al., "Synthesis of Hyper–branched Dendritic Lactosides", *Tetrahedron Letters*, vol. 36, No. 25, 1995, 4377–4380.

Ardoin and Astruc, "Molecular trees: from synthesis towards applications", *Bull. Soc. Chim. Fr.*, vol. 132, 1995, 875–909.

Sarabu et al., "Design and Synthesis of Small Molecules Interleukin–1 Receptor Antagonists based on a Benzene Template", *Drug Design and Discovery*, vol. 15, 1998, 191–198.

*Primary Examiner*—Charanjit S. Aulakh
(74) *Attorney, Agent, or Firm*—Elizabeth M. Anderson

(57) ABSTRACT

This invention is for low molecular weight dendritic polymers (dendroids) of Formula I

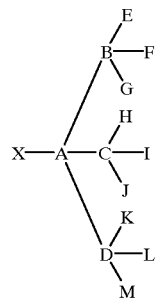

are useful as agents in the treatment of cancer, Alzheimers disease, thrombosis, inflammatory diseases, and bacterial resistance.

4 Claims, No Drawings

LOW MOLECULAR WEIGHT DENDRITIC COMPOUNDS AS PHARMACEUTICAL AGENTS

This application is a 371 of PCT/US97/11556 filed Aug. 12, 1997, now WO98/06691 Feb. 19, 1998. This application claims benefit of provisional application 60/023,693, filed Aug. 14, 1996 and 60/055,101 filed Aug. 6, 1997.

Natural biopolymers such as peptides, proteins, DNA, RNA, polysaccharides and conjugates thereof, and synthetic polymers such as polyethylene, polypropylene, and polyamides consist largely of long linear chains of covalently joined monomeric species.

Dendritic polymers are a special class of synthetic polymer that are characterized by a nonlinear array of monomeric species. Dendritic polymers may be viewed as having the structure of dendrites or trees (Greek dendron=tree).

Dendritic polymers have unique physical properties with a range of potential novel industrial applications (Review: V ögtle F., et al., *Angew. Chem. Int. Ed.*, 1994;33:2413–2420).

This invention relates to low molecular weight (<1000 daltons) dendritic compounds that offer a distinctly novel structural and chemical motif that can interact with a wide range of biologically important targets and hence have potential therapeutic utility.

SUMMARY AND DETAILED DESCRIPTION OF THE INVENTION

The low molecular weight dendritic polymers of this instant invention (herein called "dendroids") are of formula

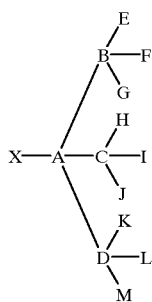

I or a pharmaceutically acceptable salt thereof wherein:

A is a "core" monomer such as 1,2,3,5-tetrasubstituted or 1,2,4- or 1,3,5-trisubstituted benzene; 2,3,4,5-tetrasubstituted or 2,3,5; or 2,4,5-trisubstituted thiophenes; 2,3,4,6- or 2,4,5,6-tetrasubstituted or 2,3,5; or 2,3,6-trisubstituted pyridine; 1,8,X-trisubstituted naphthalenes (perisubstituted naphthalene); or other such ortho- and meta-substituted aromatics or hydroaromatics.

A may also be a cyclic small hydrocarbon, such as cyclobutane, oxetane, thioxetane, azetidine, cyclopropane, or bicyclo [2.2.1]heptane, a "spiro" carbon atom, or a single nitrogen atom.

B, C, and D are covalently bonded to A, and may be identical or are independently taken from —Y—Z— when:

Y is exemplified by such "spacer" groups, but not limited to =$(CH_2)_n$—O—(n=0–3); O—$(CH_2)_n$—; —NHCO$(CH_2)_n$—; $(CH_2)_n$NHCO—; CONH—$(CH_2)_n$—; $(CH_2)_n$ CONH—; —$(CH_2)_n$—; a bond.

Z=di-, tri-, or tetrasubstituted benzene or as defined for A above or is a substituted amine, amide, carbamate, or a bond.

E through M are defined as independently taken from B through D above.

X=defined below.

Preferred dendritic compounds are:

8-(4-Bromo-benzyloxy)-naphthalene-1-carboxylic acid dimethylamide;

8-(4-Methoxy-benzyloxy)-naphthalene-1-carboxylic acid dimethylamide;

8-(3,4-Dimethoxy-benzyloxy)-naphthalene-1-carboxylic acid dimethylamide;

8-(3,4,5-Trimethoxy-benzyloxy)-naphthalene-1-carboxylic acid dimethylamide;

Benzene, 4-[[2-[(3,5-dimethoxyphenyl)methoxy]phenoxy]methyl]-1,2-dimethoxy-;

1,2-Dimethoxy-4-[[3-[3,5-dimethoxyphenyl)methoxy]phenoxy]methyl]-benzene;

Benzene, 5-[[2-[3,4-dimethoxyphenyl)-methoxy]-6-[(3,5-dimethoxyphenyl)methoxy]phenoxy]methyl]-1,2,3-trimethoxy-;

8-(3,5-Dimethoxy-benzyloxy)-naphthalene-1-carboxylic acid dimethylamide;

8-(Biphenyl-4-ylmethoxy)-naphthalene-1-carboxylic acid dimethylamide;

8-(4-Benzyloxy-benzyloxy)-naphthalene-1-carboxylic acid dimethylamide;

8-(4-Styryl-benzyloxy)-naphthalene-1-carboxylic acid dimethylamide;

8-Hydroxy-naphthalene-1-carboxylic acid benzyl-phenethyl-amide;

8-(4-Benzyloxy-benzyloxy)-naphthalene-1-carboxylic acid benzyl-phenethyl-amide;

8-(4-Benzyloxy-benzyloxy)-naphthalene-1-carboxylic acid benzyl-ethyl-amide;

8-(4-Benzyloxy-benzyloxy)-naphthalene-1-carboxylic acid [1-(1H-indol-3-yl)-ethyl])-isopropyl-amide; and 8-(4-Benzyloxy-benzyloxy)-naphthalene-1-carboxylic acid [2-(2-methoxy-phenyl)-ethyl]-phenethyl-amide.

The minimum branching array of the dendroid is given in formula in which none of B through to I is a bond.

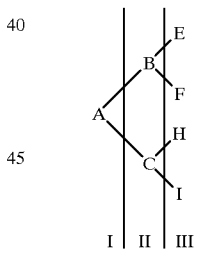

II

The Domain of A (I) is considered as the zero-order branching domain; Area II (to include B,C) is the first order domain, and Area III (to include E through I) is the second order domain.

Most compounds of MW<1000 daltons would likely fall within a second order array.

The "capping" moieties of the dendroid (B through M) essentially form a surface that is able to interact with the biological target. The nature of these capping moieties is important to determine the specificity and selectivity of the dendroid-receptor interaction.

Hence, a further embodiment of this invention is that B through M may also terminate in additional capping moieties taken from those known in the art of drug design that optimally bind to biological receptors. These include in a second order dendroid, that E, for example, may be further derivatized by P when P is taken from:

1. Side chains of the 20 genetically coded amino acids, e.g., E—$CH_2CO_2H$ (Aspartic acid side-chain mimetic); E—$(CH_2)_3NH_2$ (Lysine side-chain mimetic). P may also be attached by spacers such as Y above.

2. Heterocyclic bases of nucleotide monomers also attached by spacers such as Y. Heterocyclic bases may include guanine, uracil, adenosine, cytosine, and thymine for delivery of the dendroid to RNA and DNA targets 3. Sugar residues such as glucose, sucrose, mannose, and ribose, attached by spacers such as Y for delivery to glycoprotein and carbohydrate targets.

4. Conjugate systems of 1 to 3 above to embody glycopeptides and peptide/oligonucleotides, attached by spacers such as Y.

The spacer group Y also conveys important structural and physical properties to the molecule to create "self assembly supra molecular" topologies. (Lehn J. M., *Pure and Applied Chemistry* 1994; 66:1961–1966).

For example, when two or more of the spacers Y are composed of hydrophobic moieties (e.g., methylene groups), they are able to undergo hydrophobic collapse and hence hold the dendritic Groups B through M together in 3-dimensional space. This enhances the ability of the capping groups to form a discrete surface to interact optimally with the biological target.

When two of the spacers are composed of hydrophilic moieties (e.g., amide/reverse amide groups), they may undergo hydrophilic collapse (e.g., to form a hydrogen bond in an antiparallel planer arrangement) which may also enhance a surface formation by B through M.

Additionally, if the capping groups B through M are required to be spaced apart (e.g., 2 polar groups such as an amine and carboxylic acid), then the potential for intramolecular hydrophilic collapse (to form an intramolecular salt-bridge) can be minimized by inserting a hydrophobic moiety between them (see Compound 1 as an example, below). Dendroids should be viewed as low molecular weight monomeric species and therefore distinct from dendritic compounds which are essentially polymeric species. Hence, dendroids represent a unique vehicle for controlling the 5 critical molecular design parameters, i.e., size, shape, topology, flexibility, and surface chemistry.

The dendroids are of particular interest in the ability of the "capped surfaces" to interact with biological receptor targets where the receptor determinants are spread over a large surface area, say 400 Å$^2$.

Dendroids are expected to interact with large protein surfaces. Examples include those found between the ras/raf protein complex and other key protein/receptor complexes involved in regulation of cell growth such as Rb (retinoblastoma) and p-53 protein. the latter being a key element in the development of programmed cell death (apoptosis). Also included is the C-A-A-X motif of ras protein farnesylation, the FK-506/binding proteins complex, and cytokines such as IL-1, TNF, and IL-6, inhibition of β-amyloid protein fibrillogenesis/aggregation/deposition, and ion channels blocked by large peptides and proteins such as conotoxins, spider and snake venom.

FIG. III specifically claimed monomer precursors for A include:

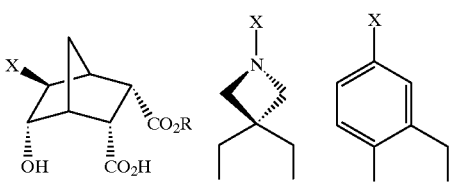

(II)

(I)

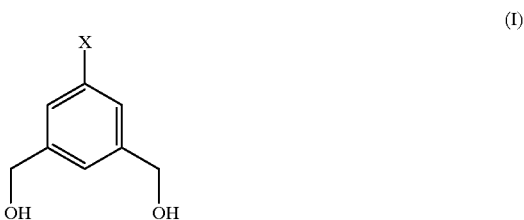

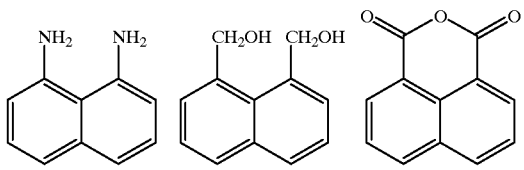

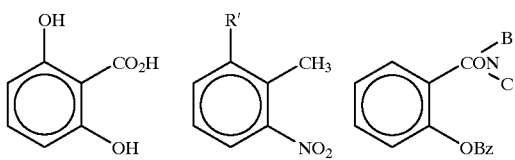

Where X=H or $(CH_2)_nCO_2R$(R=ester such as Me, Et); N=no bonds (i.e., a spiro carbon motif) or CH, N, S, or O. $R^1$=Br, OBz. B defined as above. Where the OH groups can be derivatized to give B through M as described in the literature by the same moieties (see Vögtle F., above) with Example 1, FIG. III, or by different groups by a differential protection deprotection sequence (Belle C., et al., *Tet. Letts.*, 1994:35; 7019–7022, with Example II, FIG. 3) and from the spiro or 4-membered ring moieties (Chung S. F., et al., *Bio. Med. Chem. Letts.*, 1995; 5:1091–1096, with Example III, FIG. 3).

A specific dendroid is Compound 1.

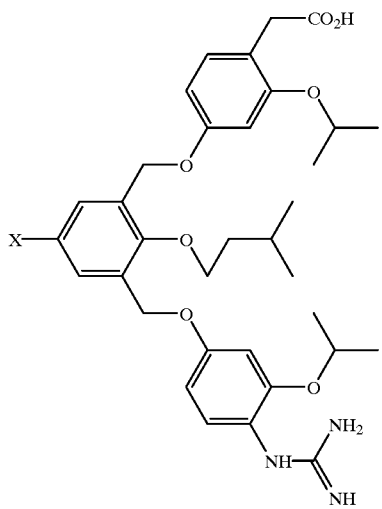

This is a dendroid whose capped surface (P=the triad

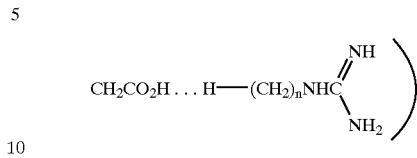

can mimic R-G-D motif found in fibrinogen antagonists (see: Ojima I., et al., Antithrombotic Agents: From RGD to Peptide Mimetics, *BioMed Chem.*, 1995; 3:337–360). This compound may be readily prepared by analogy to the published procedure to derivatize 2,6-dihydroxyl methyl phenol in the dendritic manner described by Belle, et al., above.

SCHEME 1

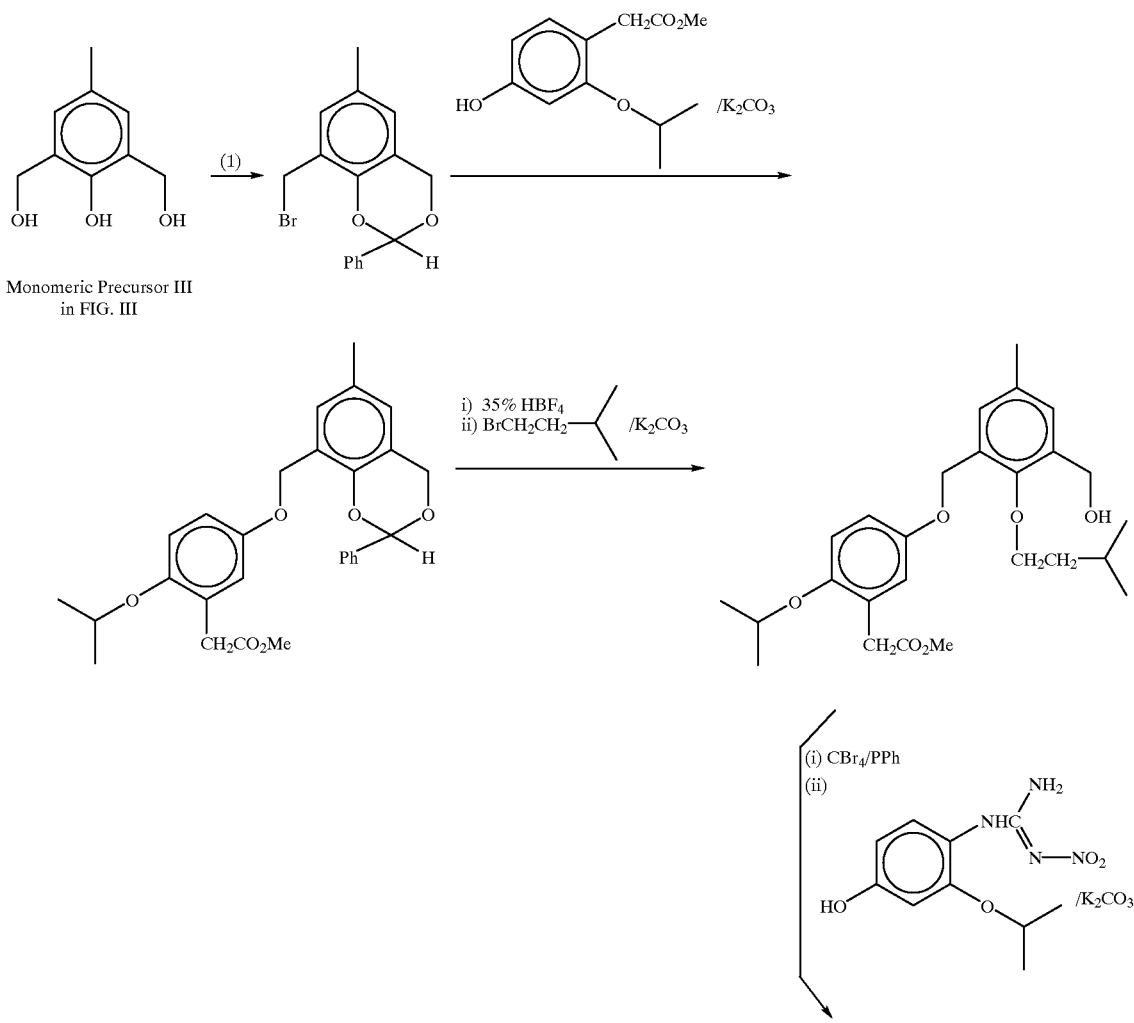

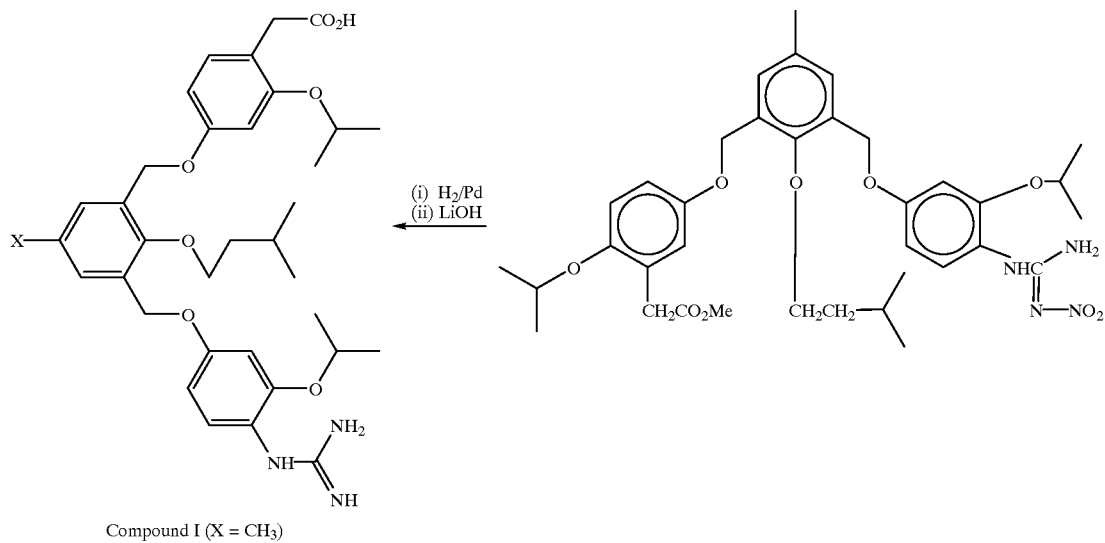

Compound I (X = CH₃)

Synthesis of Examples of Dendroids of General Structure

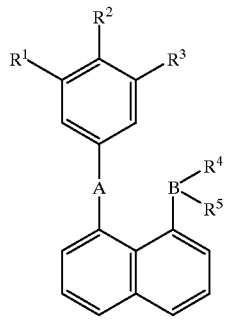

A=—C≡C—; —O—CH₂—
B=—CON—; —CO₂ (where R⁴=lone pair)
R¹=R²=R³=OMe
R¹=R³=H; R²=OMe
R¹=H; R²=R³=OMe
R¹=R³=H; R²=Br
R⁴=R⁵=Me
R⁴=lone pair; R⁵=Me
Scheme 2
A=—C≡°C—; B=—CO₂—
R¹=R³=H; R²=OMe; R⁴=lone pair;
R⁵=Me
Scheme 3
A=—OCH₂—; B=—CON—
R¹=R³=H; R²=Br; R⁴=R⁵=Me Scheme 4
As for Scheme 3 except R²=OMe
Scheme 5
As for Scheme 3 except R¹=H; R²=R³=OMe

SCHEME 2

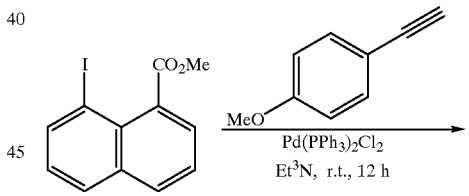

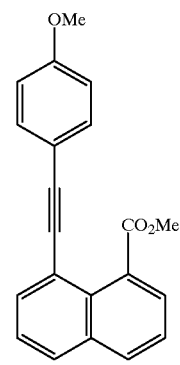

SCHEME 3
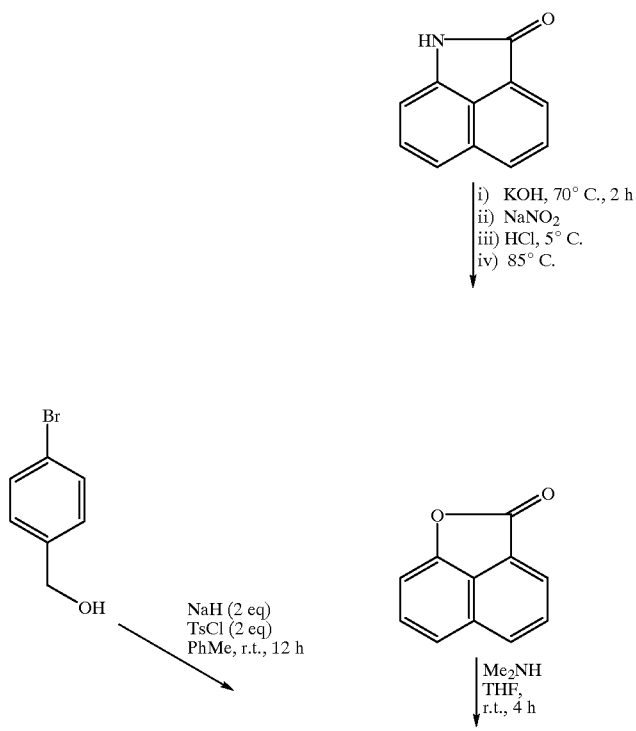
i) KOH, 70° C., 2 h
ii) NaNO$_2$
iii) HCl, 5° C.
iv) 85° C.
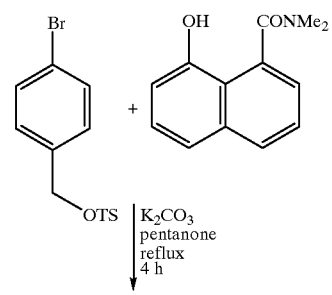
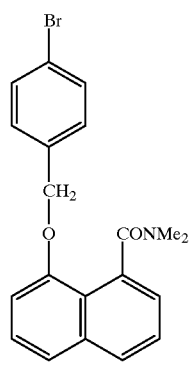

SCHEME 4
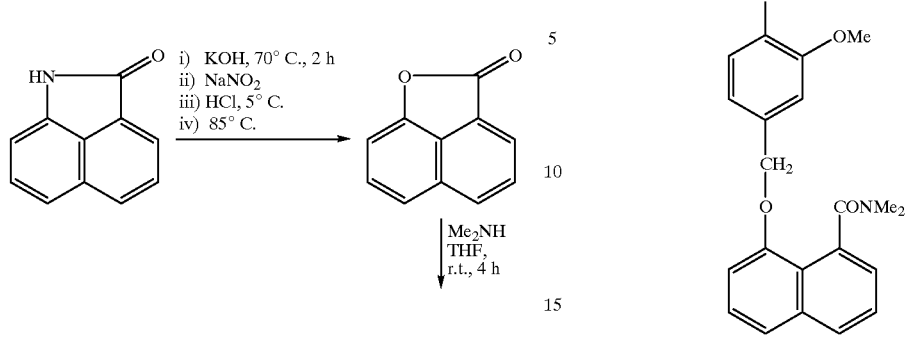
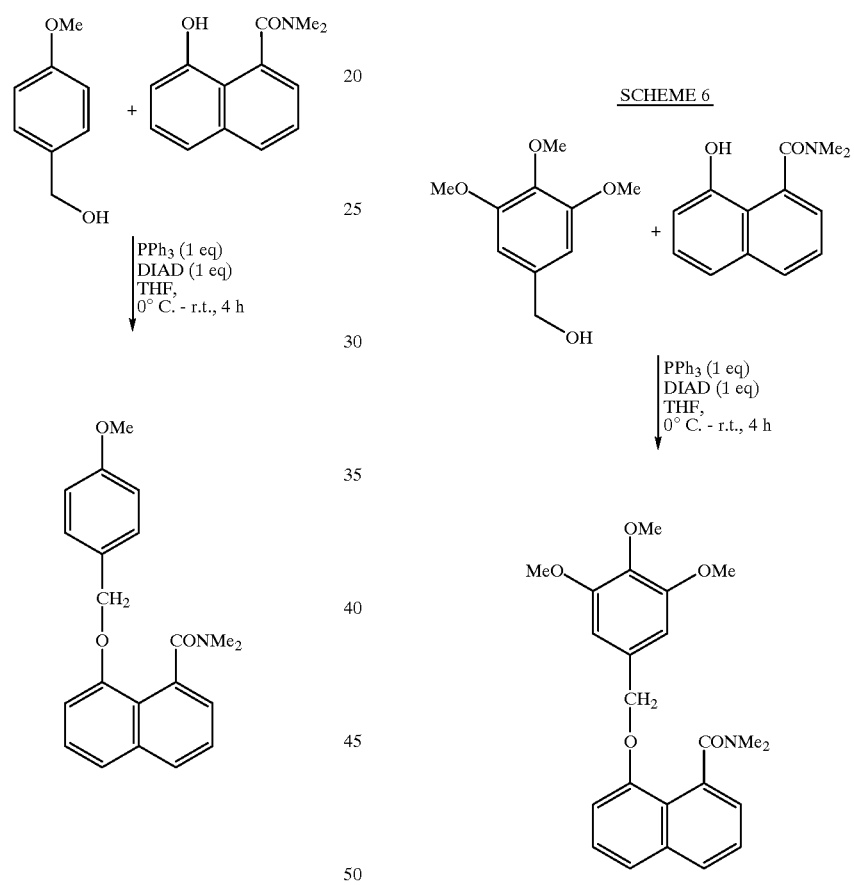
SCHEME 5
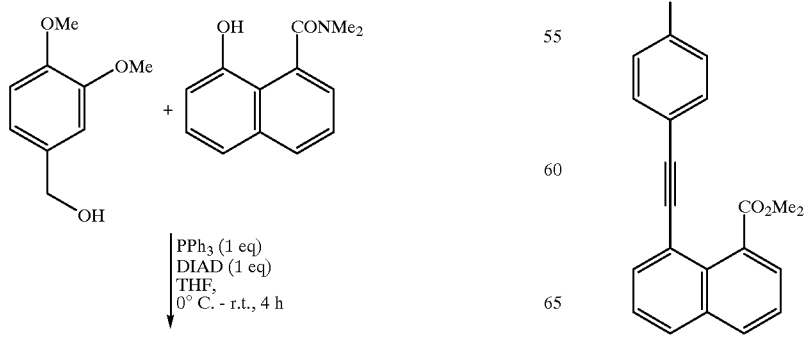

To the iodonaphthalene (50 mg, 0.16 mmol) in dry triethylamine (5 mL) was added bis(triphenylphosphine)-palladium (II) chloride (5 mg, 4 mol %), excess p-methoxyphenylacetylene (32 mg, 0.24 mmol, 1.5 eq) and a catalytic amount of cuprous iodide (3 mg, 10 mol %). The mixture was stirred under an atmosphere of nitrogen overnight at room temperature. The mixture was diluted with diethyl ether, filtered, and the solvent removed in vacuo. The residue was taken up in ethyl acetate, and the organic layer was washed successively with 0.1 M sodium hydroxide solution (aq), 0.1 M hydrochloric acid and water. The organic phase was then dried (MgSO$_4$), filtered, and the solvent removed in vacuo to give a crude product which was purified using column chromatography (silica gel, eluant-:ethyl acetate-heptane mixtures) to give the acetylene as a yellow solid (yield: 24 mg, 50%);

MS (m/z) 317 [M+1], 285, 213, 135;

$v_{max}$/cm$^{-1}$ (neat) 2950, 2838w, 2203w (C≡C), 1727vs (C=O), 1605m, 1513vs, 1462m, 1379w, 1276vs, 1250vs;

$^1$H NMR (CDCl$_3$): δ3.82 (s, 3H, OCH$_3$), 3.84 (s, 3H, CO$_2$CH$_3$), 6.90–6.92 (m, part of AA'B' system, 2H, 2'-H and 6'-H), 7.47–7.52 (m, 2H, 4-H and 5-H), 7.57–7.59 (m, part of AA'BB' system, 2H, 3'-H and 5'-H), 7.65–7.67 (dd, J=7.1 Hz, 1H, 7-H), 7.83 (app t, 2H, 3-H and 6-H), 7.92–7.94 (dd, J=8.1 Hz, 1H, 2-H);

$^{13}$C NMR (CDCl$_3$): δ52.6 (OCH$_3$), 55.4 (CO$_2$CH$_3$), 87.3 (C≡C—Ar), 95.5 (C≡C-Nap), 114.1, 115.5, 119.9, 125.2, 127.7, 129.1, 131.3, 132.1, 133.1, 133.4, 133.9, 159.8 (CO$_2$Me).

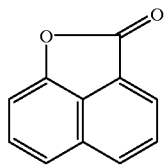

Benz[c,d]indol-2(1H)-one (50 mg, 0.3 mmol) was suspended in potassium hydroxide solution (1.12 g in 10 mL (aq), 2 M) and heated to 70° C., 2 hours. Tlc analysis after this time showed that all of the starting material had been consumed and that a very polar component (consistent with salt formation) had been produced. The solution was mixed with sodium nitrite (22 mg, 0.32 mmol, 1.1 eq), and the resulting solution was then cooled and added dropwise to a chilled (<5° C.) vessel of hydrochloric acid (1 M, aq). Once the addition was complete, the reaction mixture was heated to 85° C., 2 hours. The reaction mixture was cooled and extracted into ethyl acetate portions. The combined organic layers were washed (sodium bicarbonate (aq); brine), dried (MgSO$_4$), filtered, and concentrated in vacuo to give the crude product which was purified by column chromatography (silica gel, eluant:ethyl acetate/heptane mixtures) to give the lactone (yield: <10%);

$v_{max}$/cm$^{-1}$ (neat) 3355, 1783vs (C=O), 1472;

$^1$H NMR (CDCl$_3$): δ7.18 (m, 1H), 7.59 (m, 1H), 7.69 (m, 1H), 7.80 (m, 1H), 8.18 (m, 2H).

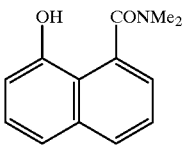

To a solution of the lactone (262 mg, 1.54 mmol) in methanol (9 mL) was added an excess of dimethylamine in solution in THF (4.62 mL of 2 M solution, 9.24 mmol, 6 eq). The reaction mixture was stirred at room temperature overnight. The methanol and any remaining dimethylamine were removed in vacuo and the crude residue taken up in ethyl acetate. The organic phase was washed (brine), dried (MgSO$_4$), filtered, and concentrated in vacuo to give the crude product which was purified by column chromatography (silica gel, eluant:ethyl acetate) to give the desired ring opened lactone, 8-hydroxynaphthalene-1-(N,N-dimethyl)-carboxamide as a tan colored solid (yield: 254 mg, 77%);

MS (m/z) 216 [M+1], 170 (M-NMe$_2$), 115;

$v_{max}$/cm$^{-1}$ (neat) 3375br (—OH stretch), 1615vs (C=O stretch in 3° amide);

$^1$H NMR (CDCl$_3$): δ2.88 (s, 3H, CH$_3$NOC), 3.18 (s, 3H, CH$_3$NOC), 7.03 (dd, J=8.1 Hz, 1H, 5-H), 7.30–7.44 (m, 4H, 7-H, 3-H, 6-H, and 4-H), 7.85 (dd, J=8.1 Hz, 1H, 2-H);

$^{13}$C NMR (CDCl$_3$): δ35.7 (NCH$_3$), 39.9 (NCH$_3$), 113.1, 120.7, 124.7, 127.2, 130.2.

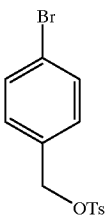

Sodium hydride (257 mg, (428 mg of 60% dispersion), 10.6 mmol, 2 eq) was added to a solution of p-bromobenzyl alcohol (1 g, 5.3 mmol) in dry toluene (30 mL). Once the concomitant effervescing had ceased, p-toluenesulphonyl chloride (2.04 g, 10.6 mmol, 2 eq) was added and the mixture stirred at room temperature, 12 hours. The toluene was removed in vacuo and the residue taken up in water and extracted into ethyl acetate portions. The combined organic layers were washed (brine), dried (MgSO$_4$), filtered, and concentrated in vacuo to give the crude product which was purified by column chromatography (silica gel, eluant:ethyl acetate/heptane mixtures) to give the p-bromobenzyl tosylate as a white solid (yield: 400 mg, 22%);

$v_{max}$/cm$^{-1}$ (neat) 1597w, 1363s (—OSO$_2$—), 1175vs (—OSO$_2$—), 1071w, 807w;

$^1$H NMR (CDCl$_3$): δ2.45 (s, 3H, ArCH$_3$), 5.00 (s, 2H, CH$_2$OTs), 7.11–7.13 (m, part of AA'BB' system on bromo ring, 2H, 2-H and 6-H), 7.32–7.33 (m, part of AA'BB' system on tosyl ring, 2H, 3'-H and 5'-H), 7.43–7.45 (m, part of AA'BB' system on bromo ring, 2H, 3-H and 5-H), 7.76–7.79 (m, part of AA'BB' system on tosyl ring, 2H, 2'-H and 6'-H);

$^{13}$C NMR (CDCl$_3$): δ21.7 (CH$_3$), 71.0 (CH$_2$), 123.3 (4'-C), 127.9 (2-C and 6-C), 129.9 (3'-C and 5'-C), 130.2 (3-C and 5-C), 131.9 (2'-C and 6'-C), 132.4 (1-C), 133.2 (4-C), 145.1 (1'-C).

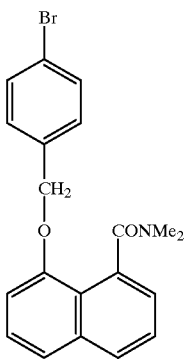

8-(4-Bromo-benzyloxy)-naphthalene-1-carboxylic Acid Dimethylamide

8-Hydroxynaphthalene-1-(N,N-dimethyl)carboxamide (235 mg, 1.09 mmol) was dissolved in dry pentanone (10 mL) under an inert atmosphere. To the solution were added successively potassium carbonate (151 mg, 1.09 mmol, 1 eq) and p-bromobenzyl tosylate (373 mg, 1.09 mmol, 1 eq). The resulting mixture was then heated to reflux, 4 hours. The mixture was cooled to room temperature, and the pentanone was removed in vacuo. The residue was taken up in ethyl acetate, and the organic layer was washed (brine), dried (MgSO$_4$), filtered, and concentrated in vacuo to give the crude product which was purified by column chromatography (silica gel, eluant:ethyl acetate/heptane mixtures) to give the ether as a white solid (yield: 241 mg, 58%);

$v_{max}$/cm$^{-1}$ (neat) 3440br, 1634vs (C=O stretch in 3° amide), 1595m, 1582m, 1462m, 1374s, 1263s, 1237m, 1173m, 1102m (C—O ether stretch);

$^1$H NMR (CDCl$_3$): δ2.59 (2×s, 6H, 2×NCH$_3$), 5.03 (d, J=10 Hz, 1H, CHHO), 5.13 (d, J=10 Hz, 1H, CHHO), 6.92–6.94 (m, 1H, 4-H), 7.27–7.29 (m, 1H, 5-H), 7.38–7.41 (m, 3H: part of AA'BB' system on bromo ring, 2H, 2'-H and 6'-H and m, 1H, 2-H), 7.45–7.49 (m, 2H, 3-H and 6-H), 7.55–7.57 (m, part of AA'BB' system on bromo ring, 2H, 3'-H and 5'-H), 7.79–7.81 (m, 1H, 7-H);

$^{13}$C NMR (CDCl$_3$): δ34.1 (NCH$_3$), 38.5 (NCH$_3$), 70.6 (CH$_2$O), 106.7, 121.7, 122.4, 124.6, 126.1, 126.3, 128.5, 130.5 (2°-C and 6'-C), 131.8 (3'-C and 5'-C), 133.2, 135.3, 154.3, 172.6 (C=O).

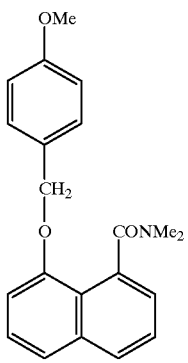

8-(4-Methoxy-benzyloxy)-naphthalene-1-carboxylic Acid Dimethylamide

To a solution of 8-hydroxynaphthalene-1-(N,N-dimethyl) carboxamide (55 mg, 0.26 mmol) and 4-methoxybenzyl alcohol (42 mg, 0.31 mmol, 1.2 eq) in dry THF (3 mL) held at 0° C. were added triphenylphosphine (67 mg, 0.26 mmol, 1 eq) and diisopropylazodicarboxylate (52 mg, 0.05 mL, 0.26 mmol, 1 eq). The mixture was stirred and allowed to warm to room temperature over several hours. The THF was removed in vacuo and the residue taken up in water and extracted into ethyl acetate portions. The combined organic layers were washed (brine), dried (MgSO$_4$), filtered, and concentrated in vacuo to give the crude product as a gummy solid, which was purified by careful column chromatography to remove the triphenylphosphine oxide by-product (silica gel, eluant:ethyl acetate/heptane mixtures) to give the Mitsunobu product as a white solid (yield: 22 mg, 25%);

$v_{max}$/cm$^{-1}$ (neat) 2933, 1717, 1634vs (C=O stretch in 3° amide), 1516, 1463, 1373, 1250, 1173, 1102, 1048;

$^1$H NMR (CDCl$_3$): δ2.48 (s, 3H, NCH$_3$), 2.58 (s, 3H, NCH$_3$), 3.83 (s, 3H, OCH$_3$), 5.01 (d, J=10 Hz, 1H, CHHO), 5.10 (d, J=10 Hz, 1H, CHHO), 6.95–6.98 (m, 3H), 7.25–7.27 (m, 1H), 7.39–7.48 (m, 5H), 7.79 (dd, J=8.1 Hz, 1H);

$^{13}$C NMR (CDCl$_3$): δ33.9 (NCH$_3$), 38.5 (NCH$_3$), 55.4 (OCH$_3$), 70.9 (OCH$_2$), 106.3, 114.0 (2'-C and 6'-C), 121.1, 121.9, 124.4, 126.0, 126.4, 128.4, 128.8, 130.6 (3'-C and 5'-C), 133.4, 135.3, 154.6, 159.8, 172.6 (C=O).

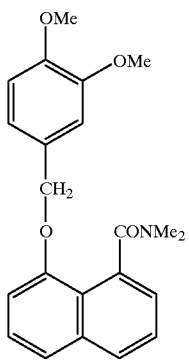

8-(3.4-Dimethoxy-benzyloxy)-naphthalene-1-carboxylic Acid Dimethylamide

To a solution of 8-hydroxynaphthalene-1-(N,N-dimethyl) carboxamide (120 mg, 0.56 mmol) and 3,4-dimethoxybenzylalcohol (94 mg, 0.56 mmol, 1 eq) in dry THF (6 mL) held at 0° C. were added triphenylphosphine (146 mg, 0.56 mmol, 1 eq) and diisopropylazodicarboxylate (113 mg, 0.12 mL, 0.56 mmol, 1 eq). The mixture was stirred and allowed to warm to room temperature over several hours. The THF was removed in vacuo and the residue taken up in water and extracted into ethyl acetate portions. The combined organic layers were washed (brine), dried (MgSO$_4$), filtered, and concentrated in vacuo to give the crude product as a gummy solid which was purified by careful column chromatography to remove the triphenylphosphine oxide by-product (silica gel, eluant:ethyl acetate/heptane mixtures) to give the Mitsunobu product as a white solid (yield: 47 mg, 23%);

$v_{max}$/cm$^{-1}$ (neat) 1716m, 1634s (C=O stretch in 3° amide) 1594m, 1516s, 1463vs, 1398, 1374, 1399, 1264, 1237;

$^1$H NMR (CDCl$_3$): δ2.46 (s, 3H, NCH$_3$), 2.55 (s, 3H, NCH$_3$), 3.91 (s, 3H, OCH$_3$), 4.03 (s, 3H, OCH$_3$), 4.97 (d, J=10 Hz, 1H, CHHO), 5.13 (d, J=10 Hz, 1H, CHHO), 6.87–6.89 (d, J=10 Hz, 1H, 6'-H), 6.96–7.01 (m, 2H, 2'-H and 5'-H), 7.20 (d, J=2 Hz, 1H), 7.27–7.29 (m, 1H), 7.40–7.49 (m, 3H), 7.80 (dd, J=8, 0.8 Hz, 1H);

$^{13}$C NMR (CDCl$_3$): δ33.9 (NCH$_3$), 38.4 (NCH$_3$), 56.0 (OCH$_3$), 56.1 (OCH$_3$), 71.2 (OCH$_2$), 106.1, 110.6, 112.9, 120.8, 121.1, 124.5, 126.0, 126.4, 128.4, 128.7, 128.9, 133.3, 135.2, 149.1, 149.2, 154.5, 172.7(C=O).

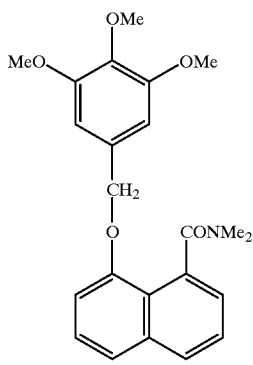

8-(3,4,5-Trimethoxy-benzyloxy)-naphthalene-1-carboxylic Acid Dimethylamide

To a solution of 8-hydroxynaphthalene-1-(N,N-dimethyl) carboxamide (55 mg, 0.26 mmol) and 3,4,5-trimethoxybenzylalcohol (61 mg, 0.31 mmol, 1.2 eq) in dry THF (3 mL) held at 0° C. were added triphenylphosphine (67 mg, 0.26 mmol, 1 eq) and diisopropylazodicarboxylate (52 mg, 0.05 mL, 0.26 mmol, 1 eq). The mixture was stirred and allowed to warm to room temperature over several hours. The THF was removed in vacuo and the residue taken up in water and extracted into ethyl acetate portions. The combined organic layers were washed (brine), dried (MgSO$_4$), filtered, and concentrated in vacuo to give the crude product as a gummy solid which was purified by careful column chromatography to remove the triphenylphosphine oxide by-product (silica gel, eluant: ethyl acetate/heptane mixtures) to give the Mitsunobu product as a white solid (yield: 24 mg, 23%);

ν$_{max}$/cm$^{-1}$ (neat) 2940, 1716w, 1634vs (C=O stretch in 3° amide), 1594, 1510, 1463, 1425, 1398, 1373, 1336;

$^1$H NMR (CDCl$_3$): δ2.53 (s, 3H, NCH$_3$), 2.56 (s, 3H, NCH$_3$), 3.87 (s, 3H, OCH$_3$), 3.97 (s, 6H, 2×OCH$_3$), 4.95 (d, J=11 Hz, 1H, CHHO), 5.17 (d, J=11 Hz, 1H, CHHO), 6.81 (s, 2H), 6.95–6.97 (m, 1H), 7.29 (dd, J=8.1 Hz, 1H), 7.41–7.51 (m, 3H), 7.82 (dd, J=7.1 Hz, 1H);

$^{13}$C NMR (CDCl$_3$): δ33.9 (NCH$_3$), 38.4 (NCH$_3$), 56.4 (2×OCH$_3$, 3'-C and 5'-C), 60.9 (OCH$_3$, 4'-C), 71.5 (CH$_2$O), 106.0, 106.2, 121.3, 121.6, 124.6, 126.1, 126.4, 128.5, 131.6, 133.2, 135.2, 137.9, 153.4, 154.4, 172.7(C=O).

Synthesis of Examples of Dendroids of General Structure

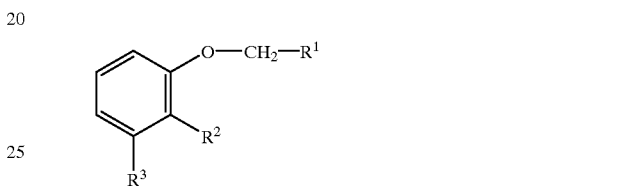

Scheme 7
R$^1$=3,4-dimethoxybenzene
R$^2$=OCH$_2$-3,5-dimethoxybenzene
R$^3$=H
Scheme 8
R$^1$=3,5-dimethoxybenzene
R$^2$=CH$_3$
R$^3$=O-CH$_2$-3,4-dimethoxybenzene
Scheme 9
R$^1$=3,5-dimethoxybenzene
R$^2$=OH
R$^3$=OCH$_2$-3,4-dimethoxybenzene

SCHEME 7

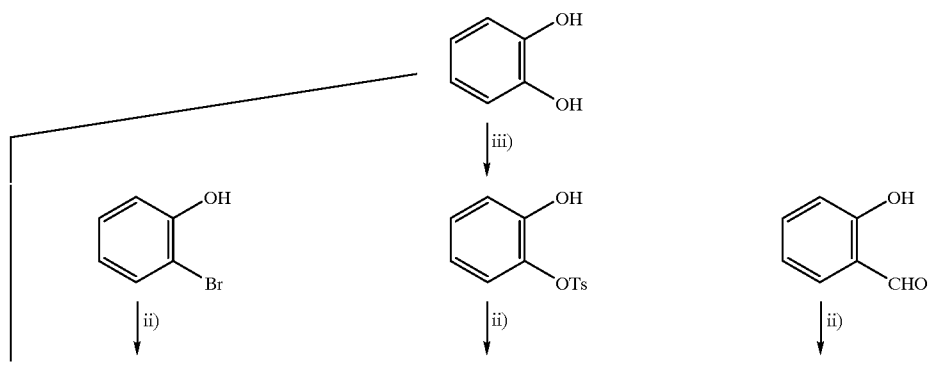

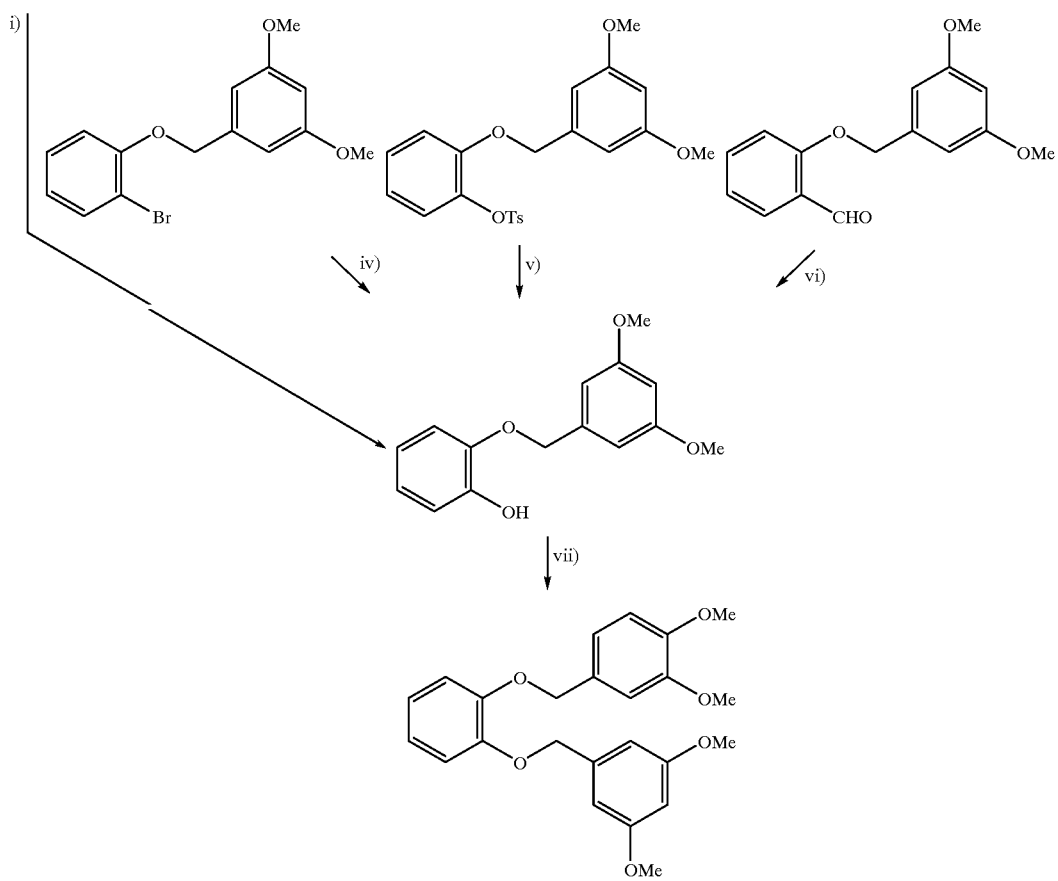

i) 4-Bromomethyl-1,3-dimethoxybenzene, K₂CO₃
ii) 4-Bromomethyl-1,3-dimethoxybenzene, K₂CO₃, 18-C-6
iii) pTsCl, K₂CO₃
iv) a. n-BuLi, B(OⁱPR)₃; b. HCl; c. H₂O₂
v) KOH, EtOH, H₂O
vi) a. m-CPBA; b. KOH
vii) 4-Bromomethyl-1,2-dimethoxybenzene, K₂CO₃

Experimental for Scheme 7

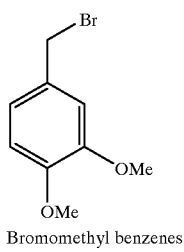

Bromomethyl benzenes

4-Bromomethyl-1.2-dimethoxybenzene

A solution of phosphorus tribromide (0.35 cm³, 3.66 mmol) in dried toluene (5 cm³) was added dropwise to a solution of 3,4-dimethoxybenzyl alcohol (1.23 g, 7.34 mmol), in dried toluene (10 cm³) at 0° C. under nitrogen. After 15 minutes, the solution was stirred at room temperature for a further 2 hours, poured onto crushed ice/water (10 cm³) and extracted with toluene (3×20 cm³). The toluene extracts were combined and washed with water (40 cm³), sodium bicarbonate (40 cm³), water (40 cm³), dried (MgSO₄), and evaporated under reduced pressure to give the bromide (1.49 g, 88%) as white needles, mp 34–37° C.

ν$_{max}$(NaCl)/cm$^{-1}$ 3002, 2958, 2936, 2835, 1605 (ArH), 1593 (ArH), 1519 (ArH), 1265, 1245, 1212, 1160, 1143;

δ$_H$ (400 MHz, CDCl₃): 3.88 (6H, d, J=7.6 Hz, 2×OMe), 4.50 (2H, s, CH₂Br), 6.80–6.96 (3H, m, ArH); bromide unstable at room temperature, therefore, no CHN or MS recorded;

Analytical HPLC grad 40–100, t$_r$=10.60 minutes, 59%.

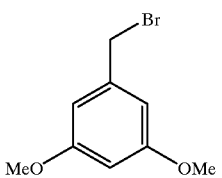

4-Bromomethyl-1,3-dimethoxybenzene

A solution of phosphorus tribromide (0.26 cm³, 2.74 mmol) in dried toluene (5 cm³) was added dropwise to a solution of 3,5-dimethoxybenzyl alcohol (1.00 g, 5.96 mmol), in dried toluene (10 cm³) at 0° C. under nitrogen.

After 15 minutes, the solution was stirred at room temperature for a further 2 hours, poured onto crushed ice/water (10 cm³), and extracted with toluene (3×20 cm³). The toluene extracts were combined and washed with water (40 cm³), sodium bicarbonate (40 cm³), water (40 cm³), dried (MgSO₄), and evaporated under reduced pressure to give the bromide (1.20 g, 87%) as white needles, mp 62–65° C. (lit 72–73° C.).

$v_{max}$(NaCl)/cm⁻¹ 3003, 2965, 2936, 2838, 1615 (ArH), 1595 (ArH), 1328, 1154, 1069, 941, 822;

$\delta_H$ (400 MHz, CDCl₃): 3.79 (6H, s, 2×OMe), 4.42 (2H, s, CH₂Br), 6.39 (1H, t, J=2.2 Hz, H4); 6.54 (2H, d, J=2.4 Hz, H-2,6);

$\delta_C$ (100 MHz, CDCl₃) 33.7 (CH₂), 55.5 (OMe), 100.7, 139.8, 161.0;

m/z (C.I.) 151 (100% M - Br), 152 (15%), 230 (16%), 231 (48% MH⁺). 233 (42%), 243 (10%);

Analysis calculated for C₉H₁₁O₂Br: C, 46.78; H, 4.80%. Found: C, 47.12; H, 4.80.

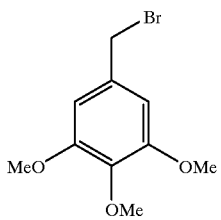

4-Bromomethyl-1.2,3-trimethoxbenzene

A solution of phosphorus tribromide (0.25 cm³, 2.63 mmol), in dried toluene (5 cm³) was added dropwise to a solution of 3,4,5-trimethoxybenzyl alcohol (1.03 g, 5.20 mmol), in dried toluene (10 cm³) at 0° C. under nitrogen. After 30 minutes, the solution was stirred at room temperature for a further 2 hours, poured onto crushed ice/water (10 cm³), and extracted with toluene (3×20 cm³). The toluene extracts were combined and washed with water (40 cm³), sodium bicarbonate (40 cm³), water (40 cm³), dried (MgSO₄), and evaporated under reduced pressure to give the bromide (1.20 g, 88%) as white needles. A small sample was recrystallized from heptane and ethyl acetate, mp 72–75° C.

$v_{max}$(NaCl)/cm⁻¹ 2940, 2838, 1589 (ArH), 1506 (ArH), 1464, 1423, 1333, 1245, 1126;

$\delta_H$ (400 MHz, CDCl₃): 3.84 (3H, s, OMe-4), 3.87 (6H, s, OMe-3,5), 4.46 (2H, s, CH₂), 6.62 (2H, s, ArH);

m/z (C.I.) 181 (100%, MH²⁺), 182 (19%), 213 (66%), 261 (2% MH⁺);

Analysis calculated for C₁₀H₁₃O₃Br: C, 46.00; H, 5.02%. Found: C, 46.09; H, 4.91.

First Alkylation

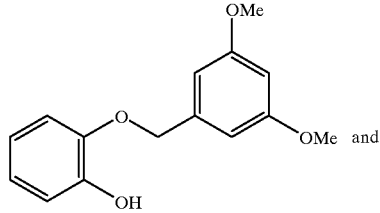

and

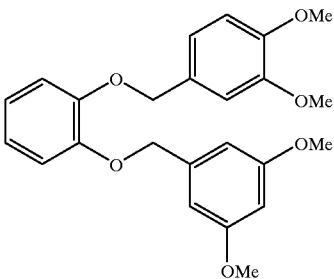

General Method 2-(3,5-Dimethoxy-benzyloxy)phenol and 1,1'-[1,2-phenylenebis(oxymethylene)]-bis[3.5-dimethoxy]-benzene] benzene Pyrocatechol (0.44 g, 3.96 mmol), 4-bromomethyl-1,3-dimethoxybenzene (0.90 g, 3.91 mmol) and potassium carbonate (0.68 g, 4.89 mmol) were heated to reflux in acetone (15 cm³, 99%) under nitrogen for 24 hours. The cooled solution was evaporated under reduced pressure, and the residue was taken up in dichloromethane (10 cm³) and water (10 cm³). The aqueous layer was extracted with dichloromethane (2×10 cm³), and the combined extracts were washed with water (2×20 cm³), dried (MgSO₄), and evaporated under reduced pressure to give an oil, mono-:di-ether, 3:1, (0.92 g, 77%);

Analytical HPLC grad 40–100, $t_r$=11.69 and 17.51 minutes, 74% and 23%.

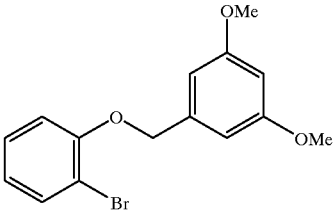

Borate Method

5-[(2-Bromophenoxy)methyl]-1.3-dimethoxybenzene

2-Bromophenol (0.31 g, 1.80 mmol), 4-bromomethyl-1, 3-dimethoxybenzene (0.28 g, 2.02 mmol), potassium carbonate (0.44 g, 1.89 mmol) and 18-crown-6-ether (0.05 g, 0.19 mmol) were stirred together at room temperature in acetone (20 cm³, 99%) under nitrogen for 15 hours. The cooled solution was evaporated under reduced pressure, and the residue was taken up in dichloromethane (10 cm³) and water (10 cm³). The aqueous layer was extracted with dichloromethane (3×10 cm³), and the combined extracts were washed with water (2×30 cm³), dried (MgSO₄), and evaporated under reduced pressure to give the bromo ether, as a clear oil (0.53 g, 92%).

$v_{max}$(film) cm⁻¹ 3064, 3000, 2938, 2838, 1599 (ArH), 1574 (ArH), 1479, 1205, 1157, 1052, 1032;

$\delta_H$ (400 MHz, CDCl₃): 3.80 (6H, d, J=1.0 Hz, OMe), 5.11 (2H, s, CH₂), 6.40 (1H, t, J=2.2 Hz, H-2(A)), 6.65 (2H, d, J=2.2 Hz, H-4,6(A)), 6.84 (1H, dt, J=1.2 Hz, 7.7, ArH), 6.92 (1H, d, J=8.1 Hz, ArH), 7.20–7.25 (1H, m, ArH), 7.55 (1H, dd, J=1.7 Hz, 7.6, ArH);

$\delta_C$ (100 MHz, CDCl₃): 55.4 (OMe), 70.7 (CH₂), 99.9, 104.7, 112.6, 114.0, 122.3, 128.5, 133.5, 139.1, 155.0, 161.1;

m/z (C.I.) 151 (100%), 152 (13%), 179 (13%), 243 (32%), 301 (12%), 323 (13% M⁺);

Analysis calculated for $C_{15}H_{15}O_3Br$: C, 55.75; H, 4.68%. Found: C, 55.81; H, 4.74.

Analytical HPLC grad 40–100, $t_r$=17.14 minutes, 82%.

2-(3.5-Dimethoxy-benzyloxy)phenol n-Butyllithium (0.66 cm$^3$, 2.5 M in hexanes, 1.65 mmol) was added to a solution of 5-[(2-bromophenoxy)methyl]-1, 3-dimethoxybenzene (0.53 g, 1.65 mmol) in dried tetrahydrofuiran (20 cm$^3$) at −78° C. under nitrogen. Triisopropyl borate (0.76 cm$^3$, 3.30 mmol) was added immediately afterwards. The solution was allowed to warm to room temperature, and after 15 hours, hydrochloric acid (20 cm$^3$, 1N) was added. After 1 hour, the solution was extracted with diethyl ether (3×40 cm$^3$). The combined extracts were washed with brine (2×100 cm$^3$), dried (MgSO$_4$), and evaporated under reduced pressure to give the crude borate, (0.47 g, 97%) as a white solid.

Hydrogen peroxide (0.64 cm$^3$, 27.5% weight in water, 5.17 mmol), and the crude borate (0.90 g, 3.24 mmol) were combined in dried tetrahydrofuran (30 cm$^3$) and heated to reflux under nitrogen for 20 hours. The cooled solution was diluted with ethyl acetate (30 cm$^3$) and washed with saturated ammonium iron (II) sulfate hexahydrate solution until no more color change occurred. The ethyl acetate layer was then dried (MgSO$_4$) and evaporated under reduced pressure. The residue was chromatographed (SiO$_2$, dichloromethane) to give the phenol, (0.51 g, 61%) as a white waxy solid, mp 55–57° C.

$v_{max}$(NaCl)/cm$^{-1}$ 3445 (OH), 2938, 2837, 1599 (ArH), 1501 (ArH), 1463, 1260, 1205, 1155, 744;

$\delta_H$ (400 MHz, CDCl$_3$): 3.80 (6H, s, OMe), 5.05 (2H, s, CH$_2$), 5.66 (1H, s, OH disappears in D$_2$O), 6.44 (1H, t, J=2.4 Hz, H-4(B)), 6.56 (2H, d, J=2 Hz, H-2,6(B)), 6.80–6.96 (4H, m, ArH);

$\delta_C$ (100 MHz, CDCl$_3$): 55.4 (OMe), 71.2 (CH$_2$), 100.2, 100.5, 105.6, 112.4, 114.9, 120.2, 122.0, 138.8, 145.8, 146.0, 161.0;

m/z (C.I.) 261 (100%, MH$^+$), 262 (13%);

Analysis calculated for $C_{15}H_{16}O_4$: C, 69.22; H, 6.20%. Found: C, 69.17; H, 6.27.

Analytical HPLC grad 40–100, $t_r$=11.69 minutes, 100%.

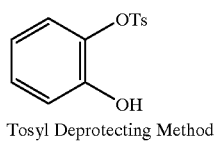

Tosyl Deprotecting Method

Toluene-4-sulfonic Acid, 2-hydroxyphenyl Ester p-Toluenesulfonyl chloride (2.88 g, 15.08 mmol) was added in two portions, 30 minutes apart, to a stirring solution of pyrocatechol (1.49 g, 13.53 mmol) and potassium carbonate (2.05 g, 14.85 mmol). The solution was heated to reflux for 4 hours. The cooled solution was evaporated under reduced pressure, and the residue was taken up in ethyl acetate (100 cm$^3$) and water (100 cm$^3$). The aqueous layer was extracted with ethyl acetate (2×100 cm$^3$), and the combined extracts were washed with brine (2×200 cm$^3$), dried (MgSO$_4$), and evaporated under reduced pressure. The residue was triturated with diethyl ether (2×20 cm$^3$), and the precipitate was removed by filtration to give unreacted toluenesulfonyl chloride (1.10 g). The filtrate was evaporated under reduced pressure. The yellow crystals were recrystallized from ethyl acetate and heptane to give mono protected pyrocatechol, (1.65 g, 53%) as clear crystalline squares, mp 80–84° C.

$v_{max}$(NaCl)/cm$^{-1}$ 3463 (OH), 3058, 1598 (ArH), 1509 (ArH), 1494 (ArH), 1369, 1179, 1160, 1088, 763;

$\delta_H$ (400 MHz, CDCl$_3$): 2.46 (3H, s, Me), 5.95 (1H, s, OH disappears with D$_2$O), 6.74–6.79 (2H, m, ArH), 6.99–7.01 (1H, m, ArH), 7.11–7.15 (1H, m, ArH), 7.35 (2H, d, J=8.0 Hz, H(A)), 7.76 (2H, d, J=8.4 Hz, H(A));

$\delta_C$ (100 MHz, CDCl$_3$): 21.9 (Me), 115.6, 118.5, 121.0, 121.3, 123.3, 128.5, 128.7, 130.1, 131.3, 137.2, 146.2, 148.5;

Analysis calculated for $C_{13}H_{12}O_4S$: C, 59.08; H, 4.58%. Found: C, 59.35; H, 4.56.

Analytical HPLC grad 40-00, $t_r$=10.79 minutes, 98%.

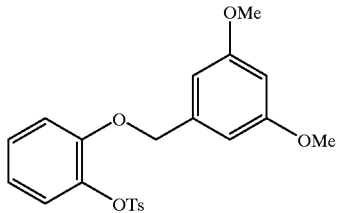

Toluene-4-sulfonic Acid 2(3,5-dimethoxy-benzyloxy) phenyl Ester

Toluene-4-sulfonic acid, 2-hydroxyphenyl ester (0.64 g, 2.42 mmol), 4-bromomethyl-1,3-dimethoxy-benzene (0.56 g, 2.42 mmol), potassium carbonate (0.36 g, 2.62 mmol) and 18-crown-6-ether (0.06 g, 0.24 mmol) were stirred together at room temperature in acetone (20 cm$^3$, 99%) under nitrogen for 28 hours. The solution was evaporated under reduced pressure, and the residue was taken up in dichloromethane (20 cm$^3$) and water (20 cm$^3$). The aqueous layer was extracted with dichloromethane (2×20 cm$^3$), and the combined extracts were washed with water (2×50 cm$^3$), dried (MgSO$_4$), and evaporated under reduced pressure. The residue was chromatographed (SiO$_2$, dichloromethane) to give the ether, (0.84 g, 83%) as a clear oil.

$v_{max}$(film)/cm$^{-1}$ 2939, 1599 (ArH), 1498 (ArH), 1196, 1181, 1158, 813, 762;

$\delta_H$ (400 MHz, CDCl$_3$): 2.40 (3H, s, Me), 3.80 (6H, s, OMe), 4.87 (2H, s, CH$_2$), 6.41 (1H, t, J=2 Hz, H-4(C)), 6.53 (2H, d, J=2.8 Hz, H-2,6(C)), 6.86–6.90 (2H, m, ArH), 7.09–7.25 (4H, m, ArH), 7.73–7.75 (2H, m, ArH);

$\delta_C$ (100 MHz, CDCl$_3$): 21.71 (Me), 55.5 (OMe), 70.5 (CH$_2$), 100.0, 104.8, 114.4, 121.0, 124.1, 128.0, 128.5, 129.5, 133.4, 138.8, 138.9, 145.0, 151.2, 161.0;

m/z (C.I.) 151 (100%), 179 (20%), 301 (13%), 415 (13% MH$^+$);

Analysis calculated for $C_{22}H_{22}O_6S$: C, 63.75; H, 5.35%. Found: C, 63.67; H, 5.31.

Analytical HPLC grad 40–100, $t_r$=17.34 minutes, 92%.

2-(3,5-Dimethoxybenzyloxy)phenol

A solution of potassium hydroxide (1.75 g, 31.26 mmol) in ethanol (30 cm$^3$, absolute) and water (30 cm$^3$) was added in portions 15 minutes apart to 1-[3,5-dimethoxy-benzyloxy]-2-[toluene-4-sulfonyloxy]benzene (0.68 g, 1.64 mmol). After heating to reflux for 1 hour, the cooled solution was neutralized with glacial acetic acid and evaporated under reduced pressure. The residue was extracted with diethyl ether (3×20 cm³), and the extracts were washed with sodium bicarbonate (40 cm³) and sodium hydroxide (3×20 cm³, 3% aqueous solution). The sodium hydroxide portion was saturated with solid carbon dioxide pellets, and the precipitate was removed by filtration to give the phenol (0.32 g, 74%).

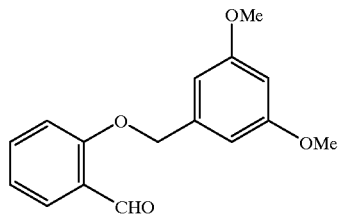

Baever Villiger Oxidation Method 2-(3,5-Dimethoxybenzyloxy)benzaldehyde

Salicylaldehyde (0.32 cm³, 3.00 mmol), 4-bromomethyl-1,3-dimethoxybenzene (0.63 g, 2.73 mmol), potassium carbonate (0.42 g, 3.00 mmol), and 18-crown-6-ether (0.07 g, 0.27 mmol) were stirred together at room temperature in acetone (50 cm³, 99%) under nitrogen for 18 hours. The solution was evaporated under reduced pressure, and the residue was taken up in dichloromethane (20 cm³) and water (20 cm³). The aqueous layer was extracted with dichloromethane (2×20 cm³), and the combined extracts were washed with water (2×50 cm³), dried (MgSO₄), and evaporated under reduced pressure. The residue was chromatographed (SiO₂, heptane:ethyl acetate, 5:1) to give a white crystalline solid. The solid was recrystallized from heptane and ethyl acetate to give the ether, (0.58 g, 78%), as white fibrous needles, mp 68–69° C.

$v_{max}$(NaCl)/cm⁻¹ 3002, 2939, 2841, 1687 (C=C), 1598 (ArH), 1457, 1240, 1205, 1158, 759;

$\delta_H$ (400 MHz, CDCl₃): 3.08 (6H, s, OMe), 5.14 (2H, s, CH₂), 6.59 (1H, t, J=2.0 Hz, H-4(B)), 6.59 (2H, d, J=2.0 Hz, H-2,6(B)), 7.01–7.06 (2H, m, ArH), 7.50–7.54 (1H, m, ArH), 7.84–7.87 (1H, m, ArH), 10.57 (1H, s, CHO);

$\delta_C$ (100 MHz, CDCl₃): 55.5 (OMe), 70.5 (CH₂), 100.0, 105.1, 113.1, 121.4, 125.3, 128.6, 136.0, 138.6, 161.0, 161.2, 189.8;

Analysis calculated for $C_{16}H_{16}O_4$: C, 70.58; H, 5.92%. Found: C, 70.78; H, 5.81.

Analytical HPLC grad 40–100, $t_r$ =13.84 minutes, 100%.

2-(3,5-Dimethoxybenzyloxy)phenol

The benzaldehyde (0.40 g, 1.47 mmol) and m-chloroperbenzoic acid (0.32 g, 1.85 mmol) were combined in dried dichloromethane (40 cm³) and heated to reflux for 8 hours. The solution was concentrated by evaporation under reduced pressure and redissolved in ethyl acetate (30 cm³). The solution was washed with sodium bicarbonate (2×80 cm³), brine (80 cm³), dried (MgSO₄), and evaporated under reduced pressure. The crude formate was taken up in methanol (30 cm³) and hydrolysed with potassium hydroxide (1.6 cm³, 10% aqueous solution, 2.88 mmol) at room temperature under nitrogen. After 4 hours, the solution was neutralized with hydrochloric acid (1N) and extracted with ethyl acetate (3×50 cm³). The extracts were washed with water (2×100 cm³), dried (MgSO₄), and evaporated under reduced pressure. The residue was chromatographed (SiO₂, ethyl acetate) to give a crude oil. The oil was taken up in diethyl ether (30 cm³) and washed with sodium hydroxide (3×30 cm³, 3% aqueous solution). The sodium hydroxide portion was saturated with solid carbon dioxide pellets, and the precipitate was removed by filtration to give the phenol (0.13 g, 33%).

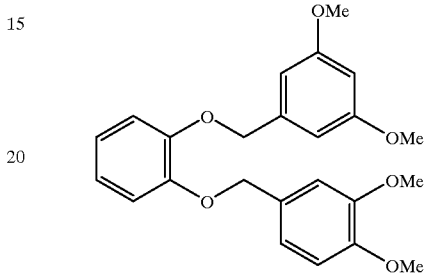

Final Alkylation

Benzene, 4-[[2-[(3,5-dimethoxyphenyl)methoxy]phenoxy]methyl]-1,2-dimethoxy-1,2-Dimethoxy-4-[[2-[(3,5-dimethoxyphenyl)methoxy]phenoxy]methyl]-benzene 2-(3,5-Dimethoxy-benzyloxy)-phenol (3:1 mono-:dialkylation mixture) (0.43 g, 1.64 mmol), 4-bromomethyl-1,2-benzene (0.38 g, 1.63 mmol) and potassium carbonate (0.28 g, 2.04 mmol) were combined in acetone (15 cm³, 99%) and heated to reflux under nitrogen for 4 days. The cooled solution was evaporated under reduced pressure, and the residue was taken up in dichloromethane (10 cm³) and water (10 cm³). The aqueous layer was extracted with dichloromethane (2×10 cm³), and the combined extracts were washed with water (2×20 cm³), dried (MgSO₄), and evaporated under reduced pressure. The residue was chromatographed (SiO₂, heptane:ethyl acetate, 3:1) to give the di ether, (0.35 g, 52%), as a white solid, mp 76–80° C.

$v_{max}$(NaCl)/cm⁻¹ 2998, 2935, 2836, 1597 (ArH), 1516 (ArH), 1505 (ArH), 1463, 1256, 1205, 1156, 1028;

$\delta_H$ (400 MHz, CDCl₃): 3.74 (6H, s, OMe), 3.82 (3H, s, OMe), 3.88 (3H, s, OMe), 5.079 (2H, s, CH₂), 5.083 (2H, s, CH₂), 6.38 (1H, t, J=2.4 Hz, H-4(C)), 6.61 (2H, d, J=2.4 Hz, H-2,6(C)), 6.82–7.04 (7H, m, ArH);

$\delta_H$ (400 MHz, CD₃OD): 3.70 (6H, s, OMe), 3.73 (3H, s, OMe), 3.76 (3H, s, OMe), 5.03 (4H, s, CH₂), 6.39 (1H, t, J=2.2 Hz, H-4(C)), 6.61 (2H, d, J=2.2 Hz, H-2,6(C)), 6.91–7.07 (7H, m, ArH);

$\delta_C$ (100 MHz, CDCl₃): 55.3 (OMe), 55.8 (OMe), 55.9 (OMe), 71.2 (CH₂), 71.4 (CH₂), 99.7, 105.0, 110.9, 111.0, 115.1, 115.4, 120.0, 121.7, 121.8, 130.0, 139.9, 148.8, 149.2, 160.9;

m/z (C.I.) 151 (100%), 152 (14%), 301 (19%), 410 (3%, MH⁺);

Analysis calculated for $C_{24}H_{26}O_6 \cdot 0.13H_2O$: C, 69.83; H, 6.41%.

Found: C, 69.84; H, 6.31.

Analytical HPLC grad 40–100, $t_r$=16.24 minutes, 94%.

SCHEME 8
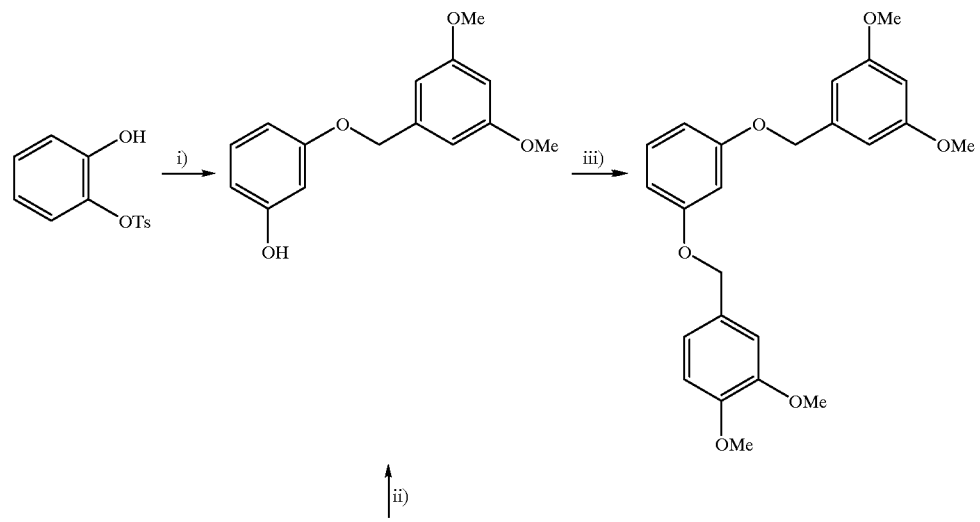
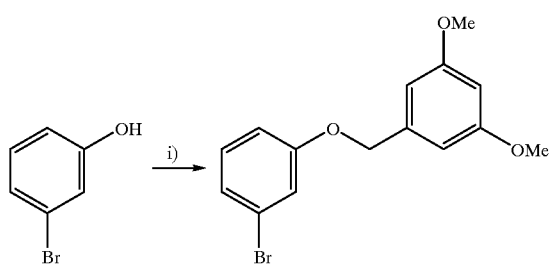
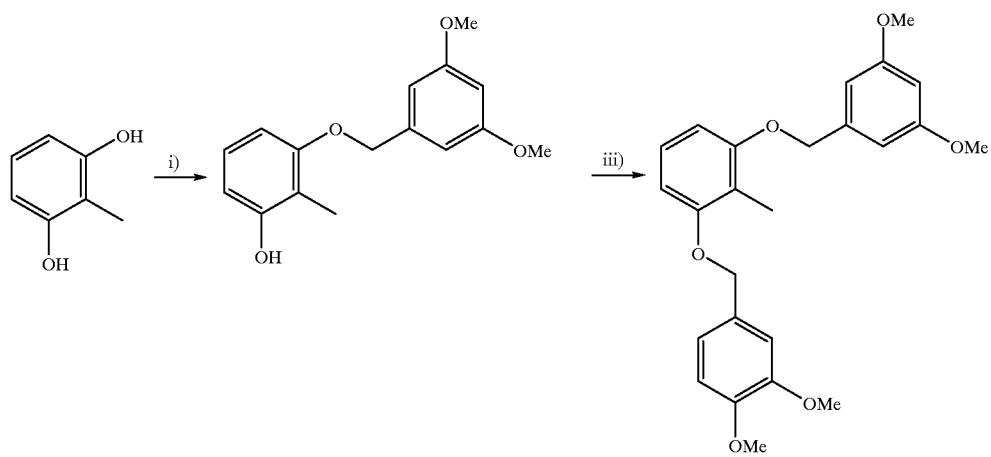
i) 4-Bromomethyl-1,3-dimethoxybenzene K$_2$CO$_3$, 18-C-6
ii) n-BuLi, B(O$^i$Pr)$_3$, HCl, H$_2$O$_2$
iii) 4-Bromomethyl-1,2-dimethoxybenzene, K$_2$CO$_3$, 18-C-6

Experimental for Scheme 8

Resorcinol Cored Dendroid
First alkylation

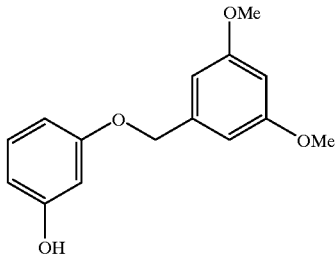

General Method

3-[3,5-Dimethoxy-benzyloxy]-phenol

Resorcinol (0.21 g, 1.87 mmol), 4-bromomethyl-1,3-dimethoxybenzene (0.39 g, 1.70 mmol), potassium carbonate (0.26 g, 1.87 mmol) and 18-crown-6-ether (0.09 g, 0.34 mmol) were stirred together in acetone (15 cm$^3$, 99%) under nitrogen at room temperature for 20 hours. The solution was evaporated under reduced pressure, and the residue was taken up in dichloromethane (10 cm$^3$) and water (10 cm$^3$). The aqueous layer was extracted with dichloromethane (2×10 cm$^3$), and the combined extracts were washed with water (2×20 cm$^3$), dried (MgSO$_4$), and evaporated under reduced pressure. The residue was chromatographed (SiO$_2$, dichloromethane) to give the phenol, (0.12 g, 27%), as an oil.

$v_{max}$(film)/cm$^{-1}$ 3405 (OH), 2996, 2939, 2840, 1597 (ArH), 1462, 1205, 1149;

$\delta_H$ (400 MHz, CDCl$_3$): 3.79 (6H, s, OMe), 4.83 (1H, s, OH disappears with D$_2$O), 4.97 (2H, s, CH$_2$), 6.41–6.58 (6H, m, ArH), 7.13 (1H, t, J=8.4 Hz, H-5(A));

m/z (C.I.) 151 (100%), 152, 179, 260, 261 (MH$^+$), 301;

Analysis calculated for C$_{15}$H$_{16}$O$_4$·0.1H$_2$O: C, 68.74; H, 6.23%.

Found: C, 68.62; H, 6.25.

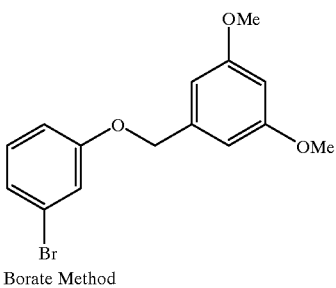

Borate Method

5-[(3-Bromophenoxy)methyl]-1,3-dimethoxy-benzene

3-Bromophenol (0.56 g, 3.25 mmol), 4-bromomethyl-1,3-dimethoxybenzene (0.76 g, 3.27 mmol), potassium carbonate (0.50 g, 3.59 mmol) and 18-crown-6-ether (0.06 g, 0.22 mmol) were stirred together at room temperature in acetone (40 cm$^3$, 99%) under nitrogen for 15 hours. The cooled solution was evaporated under reduced pressure, and the residue was taken up in dichloromethane (10 cm$^3$) and water (10 cm$^3$). The aqueous layer was extracted with dichloromethane (3×10 cm$^3$), and the combined extracts were washed with water 3×20 cm$^3$), dried (MgSO$_4$), and evaporated under reduced pressure to give the bromo ether, (1.03 g, 98%) as a clear oil.

$v_{max}$(film)/cm$^{-1}$ 3001, 2937, 2838, 1597 (ArH), 1474, 1430, 1205, 1156, 836;

$\delta_H$ (400 MHz, CDCl$_3$): 3.80 (6H, s, OMe), 4.98 (2H, s, CH$_2$), 6.41–6.43 (1H, m, H-2(A)), 6.55–6.56 (2H, m, H-4, 6(A)), 6.88–6.91 (1H, m, ArH), 7.01–7.15 (3H, m, ArH);

$\delta_C$ (100 MHz, CDCl$_3$): 55.5 (OMe), 70.2 (CH$_2$), 100.1, 105.3, 113.9, 118.3, 122.9, 124.2, 130.6, 138.8, 159.5, 161.1;

m/z (C.I.) 151 (100%), 152 (14%), 179 (10%), 243 (3%), 323 (19% M$^+$);

Analysis calculated for C$_{15}$H$_{15}$O$_3$Br: C, 55.75; H, 4.68%. Found: C, 55.81; H, 4.72.

3-[3,5-Dimethoxybenzyloxy]-phenol n-Butyllithium (1.20 cm$^3$, 2.5 M in hexanes, 3.00 mmol) was added to a solution of 5-[(3-bromophenoxy)methyl]-1,3-dimethoxybenzene (0.88 g, 2.72 mmol) in dried tetrahydrofuran (20 cm$^3$) at −78° C. under nitrogen. Triisopropyl borate (1.30 cm$^3$, 5.63 mmol) was added immediately afterwards. The solution was allowed to warm to room temperature, and after 3 hours hydrochloric acid (30 cm$^3$, 1N) was added. After 1 hour, the solution was extracted with diethyl ether (3×50 cm$^3$). The combined extracts were washed with water (2×100 cm$^3$), dried (MgSO$_4$), and evaporated under reduced pressure to give the crude borate, (0.83 g, 100%) as a yellow oil.

Hydrogen peroxide (0.53 cm$^3$, 27.5% weight in water, 4.29 mmol), and the crude borate (0.78 g, 2.70 mmol) were combined in dried tetrahydrofuran (25 cm$^3$) and heated to reflux under nitrogen for 24 hours. The cooled solution was diluted with ethyl acetate (50 cm$^3$) and washed with saturated ammonium iron (II) sulfate hexahydrate solution until no more color change occurred. The ethyl acetate layer was then dried (MgSO$_4$) and evaporated under reduced pressure. The residue was chromatographed (SiO$_2$, dichloromethane) to give the phenol (0.32 g, 45%).

Analysis calculated for C$_{15}$H$_{16}$O$_4$: C, 69.22; H, 6.20%. Found: C, 68.98; H, 6.31.

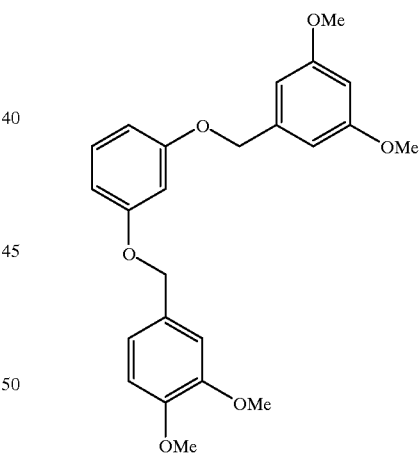

Second Alkylation 1.2-Dimethoxy-4-[[3-[3.5-dimethoxyphenyl)methoxy]phenoxy]methyl]-benzene 3-[3,5-Dimethoxybenzyloxy]-phenol (0.28 g, 1.06 mmol), 4-bromomethyl-1,2-dimethoxy-enzene (0.25 g, 1.08 mmol), potassium carbonate (0.19 g, 1.35 mmol) and 18-crown-6-ether (0.06 g, 0.23 mmol) were stirred together in acetone (15 cm$^3$, 99%) under nitrogen at room temperature for 20 hours. The solution was evaporated under reduced pressure, and the residue was redissolved in dichloromethane (10 cm$^3$) and water (10 cm$^3$). The aqueous layer was extracted with dichloromethane (2×10 cm$^3$), and the combined extracts were washed with water (2×20 cm$^3$), dried (MgSO$_4$), and evaporated under reduced pressure. The residue was chromatographed (SiO$_2$, heptane:ethyl acetate, 2:1) to give the di ether, (0.30 g, 65%), as an oil.

ν$_{max}$(film)/cm$^{-1}$ 3000, 2937, 2837, 1599 (ArH), 1519 (ArH), 1463, 1263, 1178, 1155, 1030;

δ$_H$ (400 MHz, CDCl$_3$): 3.79 (6H, s, OMe), 3.88 (3H, s, OMe), 3.89 (3H, s, OMe), 4.96 (2H, s, CH$_2$), 4.98 (2H, s, CH$_2$), 6.42 (1H, t, J=2.4 Hz, H-4(C)), 6.57–6.63 (5H, m, ArH), 6.86 (1H, d, J=8.8 Hz, ArH), 6.96 (2H, q, J=2.0 Hz, ArH), 7.18 (1H, t, J=8.0 Hz, H-5(A));

δ$_H$ (400 MHz, CD$_3$OD): 3.75 (6H, S, OMe), 3.81 (3H, s, OMe), 3.82 (3H, s, OMe), 4.96 (2H, s, CH$_2$), 4.98 (2H, s, CH$_2$), 6.41 (1H, t, J=2.4 Hz, H-4(C)), 6.55–6.60 (5H, m, ArH), 6.91–7.04 (3H, m, ArH), 7.14 (1H, t, J=8.2 Hz, H-5(A));

δ$_C$ (100 MHz, CDCl$_3$): 55.4 (Me), 55.9 (OMe), 56.0 (OMe), 70.1 (CH$_2$), 70.2 (CH$_2$), 100.0, 102.4, 105.3, 107.4, 107.5, 111.1, 111.2, 120.4, 129.4, 130.0, 139.4, 149.0, 149.2, 160.0, 160.11, 161.1, 162.0;

m/z (C.I.) 261 (24% alcohol H$^+$), 273 (100%), 302 (64%), 411 (76% MH$^+$), 424 (46%), 466 (19%), 562 (36%), 563 (13%);

Analysis calculated for C$_{24}$H$_{26}$O$_6$·0.25H$_2$O: C, 69.47; H, 6.38%.

Found: C, 69.46; H, 6.53.

Analytical HPLC grad 60–100, t$_r$=10.84 minutes, 91%.

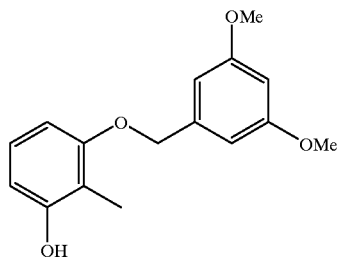

2-Methyl Resorcinol Cored Dendroid 3-(3,5-Dimethoxy-benzyloxy)-2-methyl-phenol

2-Methyl resorcinol (0.07 g, 0.59 mmol), 4-bromomethyl-1,3-dimethoxybenzene (0.13 g, 0.55 mmol), potassium carbonate (0.09 g, 0.68 mmol) and 18-crown-6-ether (0.03 g, 0.11 mmol) were combined in acetone (15 cm$^3$, 99%) and heated to reflux under nitrogen for 22 hours. The solution was evaporated under reduced pressure, and the residue was taken up in dichloromethane (10 cm$^3$) and water (10 cm$^3$). The aqueous layer was extracted with dichloromethane (2×10 cm$^3$), and the combined extracts were washed with water (2×20 cm$^3$), dried (MgSO$_4$), and evaporated under reduced pressure. The residue was chromatographed (SiO$_2$, dichloromethane) to give the phenol, (0.02 g, 15%), as a white solid, mp 63–69° C.

ν$_{max}$(NaCl)/cm$^{-1}$ 3417 (OH), 2937, 2829, 1597 (ArH), 1470, 1205, 1155, 1100, 1067;

δ$_H$ (400 MHz, CDCl$_3$): 2.19 (3H, s, Me), 3.80 (6H, s, OMe), 4.79 (1H, s, OH disappears with D$_2$O), 5.01 (2H, s, CH$_2$), 6.41 (1H, t, J=2.4 Hz, H-4(B)), 6.46 (1H, d, J=8.4 Hz, H-4 or 6(A)), 6.51 (1H, d, J=8.0 Hz, H-4 or 6(A)), 6.60 (2H, d, J=2.4 Hz, H-2,6(B)), 7.00 (1H, t, J=8.0 Hz, H-5(A)):

δ$_C$ (100 MHz, CDCl$_3$): 8.3 (Me), 55.4 (OMe), 70.2 (CH$_2$), 99.7, 104.6, 105.0, 108.4, 112.7, 126.5, 140.0, 154.6, 157.8, 161.0;

m/z (C.I.) 151 (100%), 152 (23%), 179 (11%), 275 (40% MH$^+$), 301 (4%), 425 (2%);

Analysis calculated for C$_{16}$H$_{18}$O$_4$: C, 70.06; H, 6.61%.

Found: C, 70.29; H, 6.94.

Analytical HPLC grad 60–100, t$_r$=6.65 minutes, 96%.

SCHEME 9

Preparation of Benzene, 5-[[2-[3,4-dimethoxyphenyl)-methoxy]-6-[(3,5-dimethoxyphenyl)methoxy]phenoxy]methyl]-1,2,3-trimethoxy-

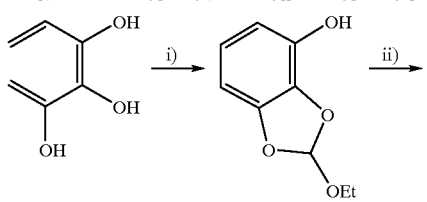

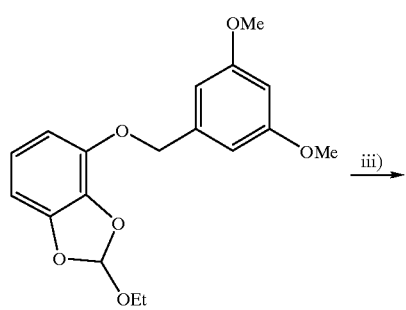

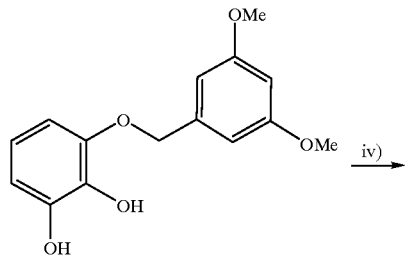

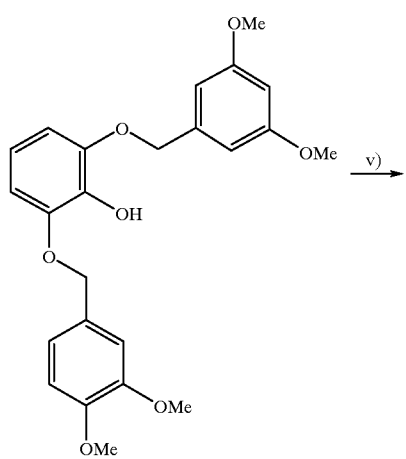

33

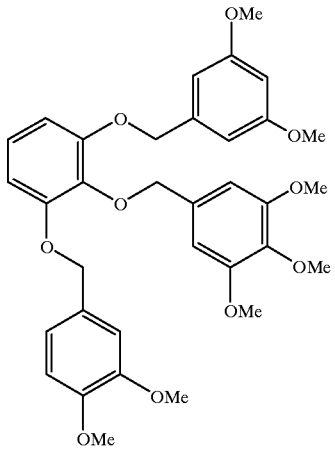

i) CH(OEt)₃, Amberlyst-IR-120(plus)
ii) 4-Bromomethyl-1,3-dimethoxybenzene, K₂CO₃, 18-C-6
iii) TsOH
iv) 4-Bromomethyl-1,2-dimethoxybenzene, K₂CO₃, 18-C-6
v) 4-Bromomethyl-1,2,3-trimethoxybenzene, K₂CO₃, 18-C-6

Experimental for Scheme 9

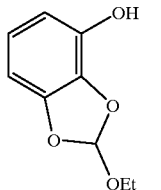

Pyrogallol Cored Dendroid

2-Ethoxy-benzo[1.3]dioxol-4-ol

Pyrogallol (0.50 g, 3.96 mmol), triethyl orthoformate (0.80 cm³, 4.81 mmol) and amberlyst-IR-120(plus), (0.11 g, 5% weight alcohol) were combined in dried toluene (40 cm³) and heated to reflux under nitrogen for 28 hours. Any low boiling solvents were removed by distillation through a 10 cm Vigreux column, and the reaction vessel was recharged with toluene as required. The cooled solution was filtered through a pad of celite, and the filtrate was evaporated under reduced pressure. The residue was filtered through a pad of silica with ethyl acetate (20% in heptane), and the filtrate was evaporated under reduced pressure to give the protected pyrogallol, (0.67 g, 92%) as clear oil.

$v_{max}$(film)/cm$^{-1}$ 3384 (OH), 2982, 1647 (ArH), 1502 (ArH), 1474, 1255, 1139, 1048, 761;

$\delta_H$ (400 MHz, CDCl₃): 1.27 (3H, t, J=7 Hz, CH₂CH₃), 3.75 (2H, q, J=7 Hz, CH₂CH₃), 4.94 (1H, br s, OH disappeared in D₂O), 6.51 (2H, dd, J=2.0, 8.0, ArH), 6.75 (1H, t, J=8.0 Hz, ArH), 6.88 (1H, s, CH);

m/z (C.I.) 108 (13%), 109 (21%), 126 (84%), 127 (100%, pyrogallol H⁺), 128 (27%);

Sample unstable, hence no $^{13}$C, CHN, HPLC.

34

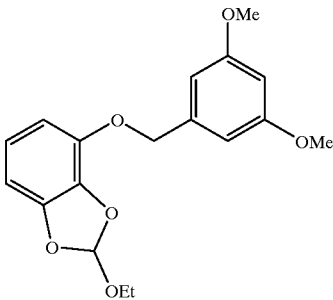

4-(3,5-Dimethoxy-benzyloxy)-2-ethoxy-benzo[1,3] dioxole

2-Ethoxy-benzo[1,3]dioxol-4-ol (1.11 g, 6.08 mmol), 4-bromomethyl-1,3-dimethoxybenzene (1.17 g, 5.08 mmol), potassium carbonate (0.77 g, 5.59 mmol) and 18-crown-6-ether (0.13 g, 0.51 mmol) were stirred together at room temperature in acetone (40 cm³, 99%) under nitrogen for 18 hours. The solution was evaporated under reduced pressure, and the residue was taken up in dichloromethane (30 cm³) and water (30 cm³). The aqueous layer was extracted with dichloromethane (3×30 cm³), and the combined extracts were washed with water (2×50 cm³), dried (MgSO₄), and evaporated under reduced pressure. The residue was chromatographed (SiO₂, dichloromethane) to give the di protected pyrogallol, (1.56 g, 92%) as a clear oil.

$v_{max}$(film)/cm$^{-1}$ 2939, 2840, 1640 (ArH), 1599 (ArH), 1501 (ArH), 1467, 1257, 1205, 1156, 1082;

$\delta_H$ (400 MHz, CDCl₃): 1.26 (3H, t, J=7.0 Hz, OCH₂CH₃), 3.70–3.76 (2H, m, OCH₂CH₃), 3.79 (6H, s, OMe), 5.14 (2H, s, CH₂), 6.39–6.40 (1H, t, J=2.0 Hz, H-4(B)), 6.54–6.59 (4H, m, ArH), 6.76 (1H, t, J=8.0 Hz, ArH), 6.89 (1H, s, CH);

$\delta_C$ (100 MHz, CDCl₃): 14.9 (Me), 55.4 (OMe), 59.3 (ether CH₂), 71.6 (CH₂), 110.0, 102.3, 105.3, 110.0, 119.1, 121.9, 134.4, 139.4, 147.4, 161.0;

m/z (C.I.) 151 (95%), 179 (33%), 259 (21%), 287 (100%, MH⁺- OEt), 332 (35% M⁺);

Analysis calculated for C₁₈H₂₀O₆: C, 65.05; H, 6.07%. Found: C, 64.92; H, 6.10.

Analytical HPLC grad 40–100, t$_r$=15.93 minutes, 95%.

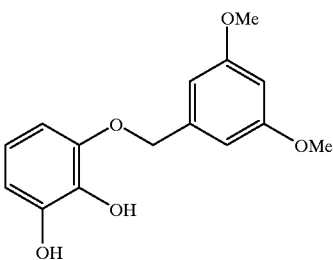

3-(3.5-Dimethoxybenzyloxy)-benzene-1,2-diol 4-(3,5-Dimethoxybenzyloxy)-2-ethoxy-benzo[1,3] dioxole (0.26 g, 0.78 mmol) and toluenesulfonic acid monohydrate (0.02 g, 0.10 mmol) were stirred together in methanol (50 cm³) at room temperature for 20 hours. The reaction was quenched by adding sodium bicarbonate (100 cm³), and the solution was concentrated by evaporation under reduced pressure. The solution was extracted with ethyl acetate (3×100 cm³), and the extracts were washed with brine (2×100 cm³), dried (MgSO₄), and evaporated under reduced pressure. The residue was chromatographed (SiO₂, heptane- :ethyl acetate, 2:1) to give the diol, (0.20 g, 90%), as white cubes, mp 75–77° C.

$\nu_{max}$(NaCl)/cm$^{-1}$ 3424 (OH), 2940, 2840, 1599 (ArH), 1504 (ArH), 1348, 1296, 1204, 1154, 1052;

$\delta_H$ (400 MHz, $CDCl_3$): 3.79 (6H, s, OMe), 5.02 (2H, s, $CH_2$), 5.39–5.44 (2H, br d, OH, disappeared in $D_2O$), 6.44 (1H, t, J=2.2 Hz, ArH), 6.50–6.60 (3H, m, ArH); 6.62 (1H, m, ArH), 6.73 (1H, t, J=8.0 Hz, ArH);

$\delta_C$ (100 MHz, $CDCl_3$) 55.5 (OMe), 71.4 ($CH_2$), 100.2, 104.7, 105.7, 109.2, 119.9, 132.9, 138.8, 144.3, 146.2, 161.2;

m/z (C.I.) 151 (100%), 152 (18%), 277 (24% $MH^+$);

Analysis calculated for $C_{15}H_{16}O_5$: C, 65.21; H, 5.84%. Found: C, 65.51; H, 5.74.

Analytical HPLC grad 40–100, $t_r$=8.85 minutes, 99%.

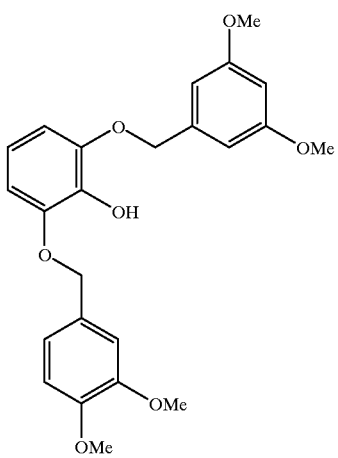

2-[3,4-Dimethoxybenzyloxy]6-[3,5-dimethoxy-benzyloxy]-phenol 3-(3,5-Dimethoxybenzyloxy)-benzene-1,2-diol (0.28 g, 1.03 mmol), 4-bromomethyl-1,2-dimethoxy-benzene (0.24 g, 1.03 mmol), potassium carbonate (0.14 g, 1.03 mmol) and 18-crown-6-ether (0.03 g, 0.11 mmol) were stirred together at room temperature in acetone (30 cm$^3$, 99%) under nitrogen for 21 hours. The solution was evaporated under reduced pressure, and the residue was taken up in dichloromethane (10 cm$^3$) and water (10 cm$^3$). The aqueous layer was extracted with dichloromethane (2×10 cm$^3$), and the combined extracts were washed with water (2×40 cm$^3$), dried ($MgSO_4$), and evaporated under reduced pressure. The residue was taken up in diethyl ether (30 cm$^3$) and washed with sodium hydroxide (2×15 cm$^3$, 3% aqueous solution). The sodium hydroxide portion was saturated with solid carbon dioxide pellets and extracted with diethyl ether (3×30 cm$^3$). The extracts were evaporated under reduced pressure to give a crude oil. The oil was chromatographed ($SiO_2$, heptane:ethyl acetate, 1:1) to give the phenol, (0.14 g, 31%) as a clear oil.

$\nu_{max}$(film)/cm$^{-1}$ 3445 (OH), 2937, 2837, 1597 (ArH), 1516 (ArH), 1464, 1266, 1205, 1157, 1065;

$\delta_H$ (400 MHz, $CDCl_3$): 3.77 (6H, s, OMe), 3.79 (3H, s, OMe), 3.88 (3H, s, OMe), 5.06 (2H, s, $CH_2$), 5.09 (2H, s, $CH_2$), 5.64 (1H, s, OH, disappeared in $D_2O$), 6.42–6.43 (1H, m, ArH), 6.54–6.58 (2H, m, ArH), 6.63 (2H, d, J=2.4 Hz, ArH), 6.82–6.98 (4H, m, ArH);

$\delta_C$ (100 MHz, $CDCl_3$): 55.4 (OMe), 55.8 (OMe), 56.0 (OMe), 70.9 ($CH_2$), 75.5 ($CH_2$),99.8, 105.3, 105.8, 108.5, 111.1, 111.9, 121.4, 124.2, 129.8, 134.9, 139.4, 149.1, 149.4, 150.1, 151.7, 161.1;

Analysis calculated for $C_{24}H_{26}O_7$: C, 67.59; H, 6.14%. Found: C, 67.75; H, 6.22.

Analytical HPLC grad 40–100, $t_r$=13.71 minutes, 86%.

1-[3 4-Dimethoxybenzyloxy]2-[3,4,5-trimethoxybenzyloxy]3-[3,5-dimethoxbenzyloxy]benzene (see Scheme 9)

2-[3,4-Dimethoxybenzyloxy]6-[3,5-dimethoxybenzyloxy] phenol (0.11 g, 0.27 mmol), 5-bromomethyl-1,2,3-trimethoxy benzene (0.07 g, 0.28 mmol), potassium carbonate (0.05 g, 0.33 mmol), and 18-crown-6-ether (0.01 g, 0.40 mmol) were stirred together at room temperature in acetone (15 cm$^3$, 99%) under nitrogen for 21 hours. The solution was evaporated under reduced pressure, and the residue was taken up in dichloromethane (10 cm$^3$) and water (10 cm$^3$). The aqueous layer was extracted with dichloromethane (2×10 cm$^3$), and the combined extracts were washed with water (2×50 cm$^3$), dried ($MgSO_4$) and evaporated under reduced pressure to give a crude oil. The oil was chromatographed ($SiO_2$, heptane/ethyl acetate, 2:1) to give as a white solid. The solid was recrystallized from heptane and ethyl acetate to give the ether (0.07 g, 46%) as white needles (mp 86–88° C.).

$\nu_{max}$ (NaCl)/cm$^{-1}$ 2938, 2829, 1595, 1515, 1463, 1422, 1375, 1333, 1299, 1238, 1205, 1156, 1127, 1099, 1028, 832, 766;

$\delta_H$ (400 MHz; $CDCl_3$): 3.69 (3H, s, OMe), 3.75 (6H, s, OMe), 3.80 (6H, s, OMe), 3.85 (6H, d, J=2.4, OMe), 5.02 (2H, s, $CH_2$), 5.04 (2H, s, $CH_2$), 5.06 (2H, s, $CH_2$), 6.40 (1H, t, J=2.0, ArH), 6.61 (2H, d, J=2.0, ArH), 6.65 (1H, s, ArH), 6.70–6.68 (2H, m, ArH), 6.74–6.77 (1H, m, ArH), 6.92–6.97 (2H, m, ArH), 7.03 (1H, d, J=1.6, ArH);

$\delta_C$ (100 MHz; $CDCl_3$): 55.4 (OMe), 55.6 (OMe), 56.0 (OMe), 56.1 (OMe), 60.9 (OMe), 71.2 ($CH_2$), 71.7 ($CH_2$), 75.0 ($CH_2$), 99.8, 104.4, 105.1, 108.3, 108.5, 110.7, 111.8, 120.8, 123.8, 130.6, 133.0, 137.6, 138.7, 139.7, 148.8, 148.9, 153.2, 153.4, 161.0;

$C_{34}H_{38}O_{10}$ requires C, 67.31; H, 6.31%; Found: C, 67.26; H, 6.20.

Analytical HPLC grad 40–100, $t_r$=17.38 min, 97%.

Examples of Dendroid Mimetic of the Conotoxin Analog SNX-III (Mimetic of the Key Triad of Amino Acids Arg[10], Leu[11], Tyr[13]) (See Nadasdi, et al., *Biochemistry,* 1995; 36:8076) Compound 11, Scheme 11.

SCHEME 10

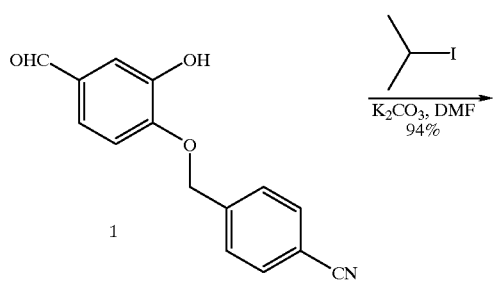
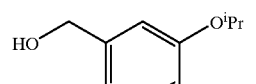
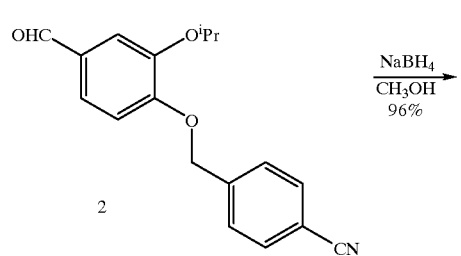
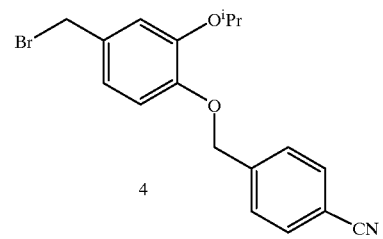
SCHEME 11
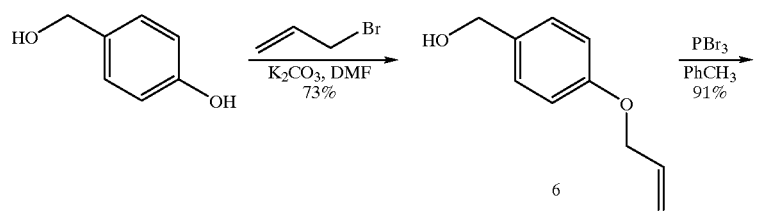
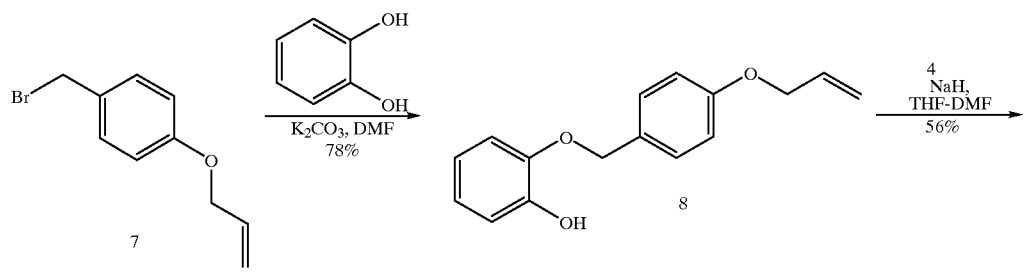
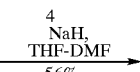

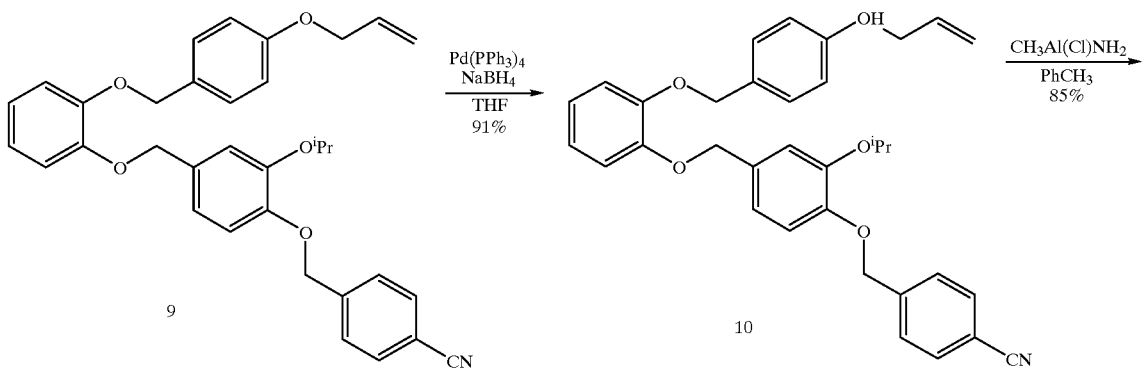

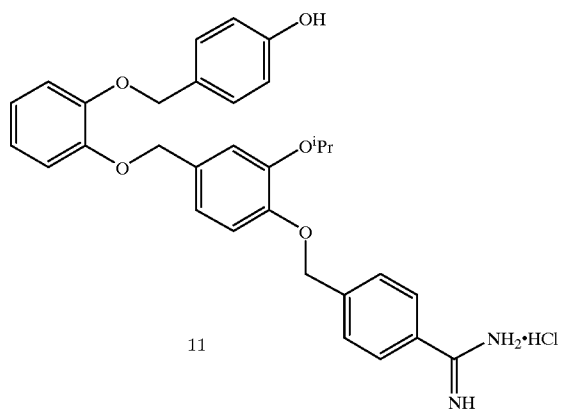

General Information

A reaction was performed under a nitrogen atmosphere unless otherwise stated. All solvents used were of analytical quality and stored over molecular sieves. All flash column chromatography purifications were performed on silica gel unless otherwise stated. All reactions were monitored using TLC analysis (silica gel/ethyl acetate:heptane, 1:1), viewing by UV and potassium permanganate dip.

1

To a solution of 3,4-dihydroxybenzaldehyde (2.0 g, 14.5 mmol) in DMF (150 mL) was added potassium carbonate (2.0 g, 14.5 mmol, 1.0 eq) and the reaction mixture stirred at room temperature for 0.5 hours. α-Bromo-p-tolunitrile (3.13 g, 15.9 mmol, 1.1 eq) was added in one portion and the reaction mixture stirred at room temperature overnight (~16 hours). The reaction mixture was quenched with water (30 mL) and diluted with ethyl acetate (50 mL). The organic extract was washed successively with 2 M HCl (2×100 mL) then water (2×100 mL), dried (MgSO$_4$), and concentrated in vacuo to a brown solid. Purification by flash column chromatography (10%–50% ethyl acetate:heptane) yielded the title compound as a colorless solid (2.85 g, 11.26 mmol, 78%).

$v_{max}$/cm$^{-1}$ 3340 (OH), 2228 (CN), 1670 (C=O).

$\delta_H$ (400 MHz, CDCl$_3$): 5.29 (2H, s, CH$_2$), 5.70 (1H, br s, OH), 6.98 (1H, d, J=8.4 Hz, ArCH), 7.41 (1H, d, J=8.4 Hz, ArCH), 7.50 (1H, s, ArCH), 7.55 (2H, d, J=8.4 Hz, ArCH), 7.73 (2H, d, J=8.4 Hz, 2×ArCH), 9.87 (1H, s, CHO); $\delta_C$ (100 MHz, CDCl$_3$/d$_6$-DMSO): 69.98, 111.91, 112.67, 113.00, 115.25, 118.56, 123.96, 127.47, 127.76, 131.04, 132.43, 141.56, 147.39, 151.48, 190.99;

m/z (C.I.) 254 (MH$^+$, 100), 139 (37), 116 (85).

2

A solution of 1 (760 mg, 3.0 mmol) and potassium carbonate (518 mg, 3.75 mmol, 1.25 eq) in DMF (60 mL) was stirred at room temperature for 0.5 hour. 2-Iodopropane (637 mg, 3.75 mmol, 1.25 eq) was added and the reaction mixture stirred for a further 2 days at room temperature. The reaction mixture was diluted with ethyl acetate (50 mL) and washed successively with 2 M HCl (2×100 mL) then water (2×100 mL), dried (MgSO$_4$), and concentrated in vacuo to a yellow oil (823 mg, 2.82, 94%). No further purification was required.

$v_{max}$/cm$^{-1}$ 2229 (CN), 1688 (C=O);

$\delta_H$(400 MHz, CDCl$_3$): 1.40 (6H, d, J=6.0 Hz, CH(CH$_3$)$_2$), 4.61–4.69 (1H, m, CH(CH$_3$)$_2$), 5.26 (2H, s, CH$_2$), 6.69 (1H, d, J=8.4 Hz, ArCH), 7.40 (1H, d, J=8.0 Hz, ArCH), 7.46 (1H, s, ArCH), 7.56 (2H, d, J=8.8 Hz, 2×ArCH), 7.69 (2H, d, J=8.4 Hz, 2×ArCH), 9.85 (1H, s, CHO);

$\delta_C$ (100 MHz, CDCl$_3$): 22.10, 69.91, 71.82, 111.98, 113.64, 118.64, 126.05, 127.32, 131.02, 132.53, 141.95, 148.62, 154.18, 190.89;

m/z (C.I.) 296 (MH$^+$, 100), 295(14), 253(12), 181 (16), 165(55), 116(90).

3

To a solution of 2 (690 mg, 2.34 mmol) in methanol (40 mL), at 0° C., was added sodium borohydride (108 mg, 2.92 mmol, 1.25 eq) portionwise. Upon completion of the addition, the reaction mixture was allowed to warm to room temperature and stirred for a further 2 hours. The reaction was quenched with water and diluted with ethyl acetate (100 mL). The organic layer was separated and the aqueous re-extracted with ethyl acetate (3×50 mL). The combined organic extracts were dried (MgSO$_4$) and concentrated in vacuo to a brown oil. Purification by flash column chromatography (10%–35% ethyl acetate:heptane) yielded the title compound as a colorless oil which solidified on standing (665 mg, 2.24 mmol, 96%).

$v_{max}$/cm$^{-1}$ (thin film) 3453 (OH), 2228 (CN); $\delta_H$ (400 MHz, CDCl$_3$): 1.37 (6H, d, J=6.0 Hz, CH(CH$_3$)$_2$), 4.51–4.57 (1H, m, CH(CH$_3$)$_2$), 4.61 (2H, s, CH$_2$), 5.17 (2H, d, J=8.0 Hz, CH$_2$), 6.84 (2H, d, J=8.4 Hz, 2×ArCH), 6.98 (1H, d, J=8.4 Hz, ArCH), 7.56 (2H, d, J=8.0 Hz, 2×ArCH), 7.66 (2H, d, J=8.4 Hz, 2×ArCH); $\delta_C$ (100 MHz, CDCl$_3$): 14.98, 22.30, 64.53, 65.14, 70.64, 71.88, 111.53, 112.66, 115.21, 115.76, 118.84, 119.37, 119.97, 127.52, 132.35, 135.32, 143.12, 148.58;

m/z (C.I.) 298 (MH$^+$, 6), 297 (26), 280 (100), 266 (67), 238 (42).

4

To a solution of 3 (660 mg, 2.22 mmol) in toluene (25 mL), at 0° C., was added phosphorus tribromide (303 mg, 1.12 mmol, 0.5 eq) in one portion. The reaction mixture was then allowed to warm to room temperature and stirred for a further 2 hours. The reaction was quenched with water and diluted with ethyl acetate (30 mL). The organic extract was washed with water 3×20 mL), then dried (MgSO$_4$) and concentrated in vacuo to a colorless solid (731 mg, 2.03 mmol, 92%). No further purification was required, and the title compound was used immediately in the reaction with 8. This compound is inherently unstable.

$v_{max}$/cm$^{-1}$ (thin film) 2228 (CN);

$\delta_H$ (400 MHz, CDCl$_3$): 1.37 (6H, d, J=6.4 Hz, CH(CH$_3$)$_2$), 4.46 (2H, s, CH$_2$Br), 4.47–4.57 (1H, m, CH(CH$_3$)$_2$), 5.17 (2H, s, CH$_2$) 6.80 (1H, d, J=8.0 Hz, ArCH), 6.89 (1H, s, ArCH), 6.98 (1H, s, ArCH), 7.54 (2H, d, J=8.4 Hz, 2×ArCH), 7.66 (2H, d, J=8.4 Hz, 2×ArCH);

m/z (C.I.) 280 (100), 266 (15), 238 (24), 181 (14), 153 (36).

6

4-Hydroxybenzyl alcohol (10.0 g, 80.6 mmol) and potassium carbonate (22.0 g, 161.3 mmol, 2 eq) in DMF (100 mL) were stirred at room temperature for 0.5 hour, before adding allyl bromide (12.1 g, 100.0 mmol, 1.2 eq). Stirring was continued at room temperature for a further 3 days. The reaction mixture was diluted with ethyl acetate (100 mL) and washed with 2 M HCl (2×100 mL) then water (2×100 mL). The organic extract was dried (MgSO$_4$) and concentrated in vacuo to a brown oil. Purification by flash column chromatography (10%–20% ethyl acetate:heptane) yielded the title compound as a yellow oil which solidified on standing (9.6 g, 58.9 mmol, 73%).

$v_{max}$/cm$^{-1}$ (thin film) 3311 (OH);

$\delta_H$ (400 MHz, CDCl$_3$): 4.54 (2H, d, J=4.8 Hz, OCH$_2$CH=), 4.61 (2H, d, J=5.6 Hz, CH$_2$OH), 5.29 (1H, d, J=10.4 Hz, =CHH'), 5.41 (1H, d, J=17.4 Hz, =CHH'), 6.01–6.10 (1H, m, =CH), 6.90 (2H, d, J=83.8 Hz, 2×ArCH), 7.28 (2H, d, J=8.8 Hz, 2×ArCH);

m/z (C.I.) 165 (MH$^+$, 16), 164 (59), 147 (100), 135 (77), 119 (9), 107 (31).

7

To a solution of 6 (4.0 g, 24.4 mmol) in toluene (150 mL), at 0° C., was added phosphorus tribromide (3.3 g, 12.2 mmol, 0.5 eq) in one portion. The reaction mixture was then allowed to warm to room temperature and stirred for a further 2 hours. The reaction was quenched with water and diluted with ethyl acetate (30 mL). The organic extract was washed with water 3×20 mL), then dried (MgSO$_4$), and concentrated in vacuo to yield the title compound as a colorless solid (5.4 g, 22.0 mmol, 91%). No further purification was required, and the title compound was used immediately in the reaction with 8. This compound is inherently unstable.

$\delta_H$ (400 MHz, CDCl$_3$): 4.49 (2H, s, CH$_2$) 4.52 (2H, d, J=5.2 Hz, CH$_2$), 5.29 (1H, d, J=10.4 Hz, =CHH'), 5.41 (1H, d, J=17.2 Hz, =CHH'), 6.01–6.08 (1H, m, =CH), 6.87 (2H, d, J=8.8 Hz, 2×ArCH), 7.31 (2H, d, J=8.8 Hz, 2×ArCH).

8

To a solution of sodium hydride (617 mg, 25.7 mmol) in THF (100 mL), at 0° C., was added the catechol (2.83 g, 25.7 mmol) in one portion. The reaction flask was then allowed to warm to room temperature and stirring continued until all H$_2$ evolution had ceased (~0.5 hour). The benzyl bromide (5.0 g, 20.6 mmol) in DMF (100 mL) was then added dropwise over 20 minutes. Upon completion of the addition, the reaction mixture was heated under reflux for 2 days. The reaction was quenched with water and diluted with ethyl acetate (100 mL), and the organics were washed successively with water (100 mL), 2 M HCl (2×100 mL), then water (2×50 mL). The organic extract was dried (MgSO$_4$) and concentrated in vacuo to yield a yellow oil. Purification by flash column chromatography yielded the title compound as a colorless oil which solidified on standing (4.8 g, 16.1 mmol, 78%).

$v_{max}$/cm$^{-1}$ (thin film) 3527 (OH);

$\delta_H$ (400 MHz, CDCl$_3$): 4.56 (2H, d, J=5.2 Hz, =CHCH$_2$O), 5.03 (2H, s, CH$_2$OAr), 5.30 (1H, d, J=10.8 Hz, =CHH'), 5.42 (1H, d, J=17.2 Hz, =CHH'), 5.64 (1H, br s, OH), 6.01–6.11 (1H, m, =CH), 6.83–6.95 (6H, m, 6×ArCH), 7.33 (2H, d, J=8.0 Hz, 2×ArCH);

m/z (C.I.) 257 (MH$^+$, 4), 148 (39), 147 (100), 123 (10),107 (15).

9

To a solution of sodium hydride (62 mg, 2.6 mmol) in THF (20 mL), at 0° C., was added 8 (685 mg, 2.52 mmol) in one portion, then reaction mixture was slowly allowed to warm to room temperature. After all H$_2$ evolution had ceased (~20 minutes), 4 (725 mg, 2.01 mmol) as a solution in DMF (20 mL) was slowly added. Upon completion of the addition, the reaction mixture was heated under reflux for 3 days. The reaction was quenched with water and diluted with ethyl acetate (50 mL). The organic extract was washed successively with 2 M HCl (2×80 mL), then water (2×80 mL), dried (MgSO$_4$), and concentrated in vacuo to a brown oil. Purification by flash column chromatography yielded the title compound as a colorless solid (617 mg, 1.12 mmol, 56%). The title compound was recrystallized from ethyl acetate/heptane.

$v_{max}$/cm$^{-1}$ (thin film) 2228 (CN);

$\delta_H$ (400 MHz, CDCl$_3$): 1.31 (6H, d, J=6.4 Hz, CH(CH$_3$)$_2$), 4.42–4.52 (1H, m, CH(CH$_3$)$_2$), 4.53 (2H, d, J=5.2 Hz, CH$_2$), 5.05 (2H, s, CH$_2$), 5.06 (2H, s, CH$_2$), 5.15 (2H, s, CH$_2$), 5.28 (1H, d, J=10.4 Hz, =CHH'), 5.40 (1H, d, J=17.3 Hz, =CHH'), 6.01–6.10 (1H, m, =CH), 6.82–6.95 (8H, m, 8×ArCH), 7.06 (1H, s, ArCH), 7.34 (2H, d, J=8.8 Hz, 2×ArCH), 7.55 (2H, d, J=8.0 Hz, 2×ArCH), 7.64 (2H, d, J=8.0 Hz, 2×ArCH);

$\delta_C$ (100 MHz, CDCl$_3$): 22.23, 68.89, 70.64, 71.09, 71.18, 71.72, 114.74, 115.31, 115.56, 115.64, 116.08, 117.76, 120.41, 121.61, 121.81, 127.51, 129.07, 129.65, 131.69, 132.35, 133.28, 143.13, 148.67, 149.24, 158.39;

m/z (C.I.). 535 (MH$^+$, 1), 419 (3), 388 (45), 255 (100).

10

To a solution of 9 (52 mg, 0.1 mmol) in THF (5 mL) was added tetrakis(triphenylphosphine)palladium (0) (2.5 mg, 0.002 mmol, 2 mol %) and the solution stirred at room temperature for 10 minutes. Sodium borohydride (6 mg, 0.15 mmol, 1.5 eq) was then added and stirring continued overnight (~16 hours). The reaction mixture was quenched with water and diluted with ethyl acetate (10 mL). The organic extract was washed with water (20 mL), dried (MgSO$_4$), and concentrated in vacuo to a yellow oil (xx mg, xx mmol, xx %).

$v_{max}$/cm$^{-1}$ (thin film);

$\delta_H$ (400 MHz, CDCl$_3$): 1.31 (6H, d, J=6.0 Hz, CH(CH$_3$)$_2$), 4.45–4.49 (1H, m, CH(CH$_3$)$_2$), 5.04 (4H, s, 2×CH$_2$), 5.15 (2H, s, CH$_2$) 6.80–6.95 (8H, m, 8×ArCH), 7.29 (2H, d, J=8.4 Hz, 2×ArCH), 7.54 (2H, d, J=8.4 Hz, 2×ArCH), 7.65 (2H, d, J=8.4 Hz, 2×ArCH);

m/z (C.I.) 280 (29), 266 (4), 123 (7), 107 (100). (APCI) 495 (1), 478 (1), 435 (1), 280 (100), 237 (7).

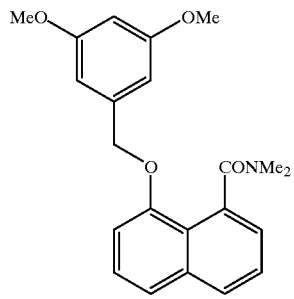

8-(3 5-Dimethoxy-benzyloxy)-naphthalene-1-carboxylic Acid Dimethylamide

To a solution of 8-hydroxynaphthalene-1-(N,N-dimethyl) carboxamide (102 mg, 0.47 mmol) in dry DMF (3 mL) was added sodium hydride (12 mg, 0.52 mmol, 1.1 eq). The sodium hydride was added as 21 mg of a 60% dispersion in mineral oil that had been previously washed with 3×heptane portions under an inert atmosphere. The mixture was stirred for 30 minutes at room temperature and 3,5-dimethoxybenzyl chloride (97 mg, 0.52 mmol, 1.1 eq) was added. The resulting mixture was stirred at room temperature overnight. The reaction mixture was poured onto ice, and the aqueous-DMF layer was extracted into ethyl acetate portions. The combined organic layers were washed (brine), dried (MgSO$_4$), filtered and concentrated in vacuo. The crude product was purified by column chromatography (silica gel, eluant:ethyl acetate/heptane mixtures) to give the desired ether (yield: 94 mg, 0.26 mmol, 55%);

$v_{max}$/cm$^{-1}$ (neat) 2938m, 1636vs (C=O in CONMe$_2$), 1611s, 1599s, 1512m, 1461m, 1398m, 1373m, 1339m, 1153s;

$^1$H NMR (CDCl$_3$): $\delta_H$ 2.57 (s, 3H, NCH$_3$), 2.58 (s, 3H, NCH$_3$), 3.85 (s, 6H, 2×OCH$_3$), 4.94 (d, J=10.8 Hz, 1H, CHHO), 5.14 (d, J=10.8 Hz, 1H, CHHO), 6.44 (t, 1H, Ar-H), 6.94–6.70 (m, 2H, 2×Ar-H), 7.28 (dd, J=7.2, 1.2 Hz, 1H, Ar-H), 7.37–7.44 (m, 1H), 7.46–7.48 (m, 2H), 7.79 (dd, J=8.4, 1.2 Hz, 1H);

$^{13}$C NMR (CDCl$_3$): $\delta_C$ 34.0 (Me in CONMe$_2$), 38.5 (Me in CONMe$_2$), 55.6 (2×OMe), 71.3 (CH$_2$O), 100.7, 106.3, 106.4, 121.3, 121.7, 124.5, 126.1, 126.4, 128.5, 133.3, 135.2, 138.4, 154.4, 160.9 (2×COMe), 172.2 (C=O in CONMe$_2$);

m/z (C.I.) 366 [M+1];

Found C, 72.4; H, 5.5; N, 3.7. C$_{22}$H$_{23}$NO$_4$ requires: C, 72.31; H, 6.34; N, 3.83%.

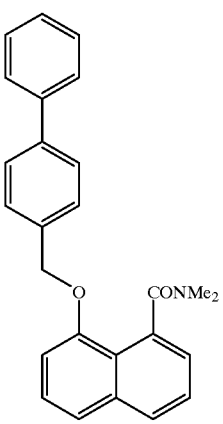

8-(Biphenyl-4-ylmethoxy)-naphthalene-1-carboxylic Acid Dimethylamide

To a solution of 8-hydroxynaphthalene-1-(N,N-dimethyl) carboxamide (68 mg, 0.32 mmol) in dry DMF (4 mL) was added sodium hydride (8 mg, 0.35 mmol, 1.1 eq). The sodium hydride was added as 14 mg of a 60% dispersion in mineral oil that had been previously washed with 3×heptane portions under an inert atmosphere. The mixture was stirred for 30 minutes at room temperature and 1-chloro-(4-biphenyl)methanol (71 mg, 0.35 mmol, 1.1 eq) was added. The resulting mixture was stirred at room temperature overnight. The reaction mixture was poured onto ice/water (100 mL), and the aqueous-DMF layer was extracted into ethyl acetate portions. The combined organic layers were washed (brine), dried (MgSO$_4$), filtered and concentrated in vacuo. The crude product was purified by column chromatography (silica gel, eluant:ethyl acetate/heptane mixtures) to give the desired ether (yield: 99 mg, 0.25 mmol, 79%);

$v_{max}$/cm$^{-1}$ (neat) 2925w, 1636 vs (C=O in CONMe$_2$), 1580w, 1510m, 1488m, 1461m, 1374m, 1338w, 1261s, 1050m;

$^1$H NMR (CDCl$_3$): $\delta_H$ 2.54 (s, 3H, NCH$_3$), 2.61 (s, 3H, NCH$_3$), 5.12 (d, J=10.8 Hz, 1H, CHHO), 5.23 (d, J=10.8 Hz, 1H, CHHO), 6.99–7.01 (app m, 1H, Ar-H), 7.28 (dd, J=7.2, 1.2 Hz, 1H, Ar-H), 7.37–7.50 (m, 6H, 6×Ar-H), 7.58–7.64 (m, 2H), 7.67–7.69 (m, 2H), 7.81 (dd, J=8.4, 1.0 Hz, 1H);

$^{13}$C NMR (CDCl$_3$): $\delta_C$ 33.9 (Me in CONMe$_2$), 38.5 (Me in CONMe$_2$), 71.1 (CH$_2$O), 106.6, 121.3, 121.8, 124.5, 126.4, 127.2, 127.4, 127.5, 123.4, 128.9, 129.4, 133.3, 135.3, 140.8, 141.3, 154.6, 172.6 (C=O in CONMe$_2$);

m/z (C.I.) 382 [M+1], 167; C$_{26}$H$_{23}$NO$_2$ requires:

Found C, 79.11; H, 5.71; N, 3.62. C, 78.56; H, 5.83; N, 3.52%.

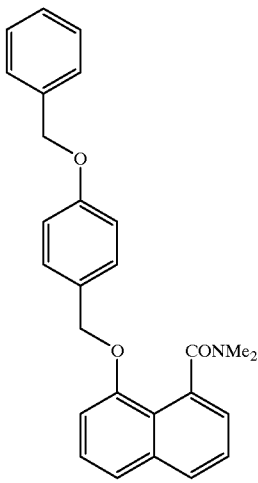

8-(4-Benzyloxy-benzyloxy)-naphthalene-1-carboxylic Acid Dimethylamide

To a solution of 8-hydroxynaphthalene-1-(N,N-dimethyl) carboxamide (100 mg, 0.46 mmol) in dry DMF (4 mL) was added sodium hydride (12 mg, 0.51 mmol, 1.1 eq). The sodium hydride was added as 20 mg of a 60% dispersion in mineral oil that had been previously washed with 3×heptane portions under an inert atmosphere. The mixture was stirred for 30 minutes at room temperature and 4-benzyloxybenzyl chloride (121 mg, 0.52 mmol, 1.13 eq) was added. The resulting mixture was stirred at room temperature overnight. The reaction mixture was poured onto ice/water (100 mL), and the aqueous-DMF layer was extracted into ethyl acetate portions. The combined organic layers were washed (brine), dried (MgSO$_4$), filtered and concentrated in vacuo. The crude product was purified by column chromatography (silica gel, eluant:ethyl acetate/heptane mixtures) to give the desired ether (yield: 146 mg, 0.35 mmol, 77%);

$v_{max}$/cm$^{-1}$ (neat) 2927m, 1637vs (C=O in CONMe$_2$), 1583m, 1514s, 1461m, 1399m, 1374m, 1338w, 1261s, 1237s;

$^1$H NMR (CDCl$_3$): $\delta_H$ 2.44 (s, 3H, NCH$_3$), 2.56 (s, 3H, NCH$_3$), 4.99 (d, J=10.4 Hz, 1H, CHHO), 5.08 (d, J=10.4 Hz, 1H, CHHO), 5.11 (s, 2H, CH$_2$O-Ph), 6.95–6.97 (m, 1H, Ar-H), 7.03–7.06 (m, 2H, part of AA'BB' system), 7.26 (dd, J=7.0, 1.4 Hz, 1H, Ar-H), 7.31–7.47 (m, 10H, 10×Ar-H), 7.79 (dd, J=8.2, 1.0 Hz, 1H);

$^{13}$C NMR (CDCl$_3$): $\delta_C$ 33.9 (Me in CONMe$_2$), 38.5 (Me in CONMe$_2$), 70.1 (CH$_2$O), 70.9 (CH$_2$O), 106.4, 115.1, 121.1, 121.8, 124.4, 126.0, 126.4, 127.5, 128.1, 128.4, 128.7, 130.7, 133.4, 135.3, 137.0 (1-C), 154.6 (4'-C), 158.9 (8-C), 172.6 (C=O in CONMe$_2$);

m/z (CI) 412 [M+1], 197; C$_{27}$H$_{25}$NO$_3$ requires:

Found C, 78.41; H, 5.83; N, 3.39. C, 78.81; H, 6.12; N, 3.40%.

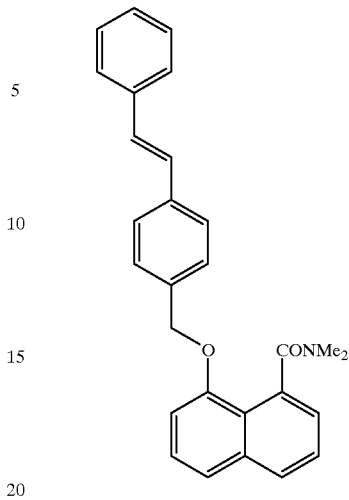

8-(4-Styryl-benzyloxy)-naphthalene-1-carboxylic Acid Dimethylamide

To a solution of 8-hydroxynaphthalene-1-(N,N-dimethyl) carboxamide (100 mg, 0.46 mmol) in dry DMF (4 mL) was added sodium hydride (12 mg, 0.51 mmol, 1.1 eq). The sodium hydride was added as 20 mg of a 60% dispersion in mineral oil that had been previously washed with 3×heptane portions under an inert atmosphere. The mixture was stirred for 30 minutes at room temperature, and 4-chloromethylstilbene (117 mg, 0.51 mmol, 1.1 eq) was added. The resulting mixture was stirred at room temperature overnight. The reaction mixture was poured onto ice/water (100 mL) and the aqueous-DMF layer was extracted into ethyl acetate portions. The combined organic layers were washed (brine), dried (MgSO$_4$), filtered and concentrated in vacuo. The crude product was purified by column chromatography (silica gel, eluant:ethyl acetate/heptane mixtures) to give the desired ether (yield: 108 mg, 0.27 mmol, 58%);

$v_{max}$/cm$^{-1}$ (neat) 2925w, 1635vs (C=O in CONMe$_2$), 1512m, 1461w, 1338w, 1261s, 1172m, 1049m, 966w, 823m;

$^1$H NMR (CDCl$_3$): $\delta_H$ 2.54 (s, 3H, NCH$_3$), 2.60 (s, 3H, NCH$_3$), 5.08 (d, J=10.8 Hz, 1H, CHHO), 5.19 (d, J=10.8 Hz, 1H, CHHO), 6.98 (app d, J=7.6 Hz, 1H, naphthyl), 7.14 (d, J=1.6 Hz, 2H, 2×vinyl), 7.28 (dd, J=7.0, 1.4 Hz, 1H, Ar-H), 7.36–7.60 (m, 12H, 12×Ar-H), 7.81 (dd, J=8.2, 1.0 Hz, 1H, naphthyl);

$^{13}$C NMR (CDCl$_3$): $\delta_C$ 34.0 (Me in CONMe$_2$), 38.5 (Me in CONMe$_2$), 69.3, 71.1, 106.5, 121.3, 121.8, 124.5, 126.0, 126.4, 126.6, 126.7, 127.8, 128.2, 128.4, 128.8, 129.1, 129.4, 133.3, 135.3, 135.5, 137.2, 137.5, 154.6, 172.6(C=O in CONMe$_2$);

m/z (C.I.) 407 M+;

Found C, 81.96; H, 5.94; N, 3.56. C$_{28}$H$_{25}$NO$_2$ requires: C, 82.53; H, 6.18; N, 3.44%.

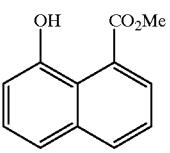

1,2-Dihydro-1-oxaacenaphthene-2-one (530 mg, 3.11 mmol) was dissolved in dry methanol (20 mL, excess) under an inert atmosphere and then left to stir at room temperature for 4 days. The methanol was then removed in vacuo leaving a crude residue which was purified by column chromatography (silica gel, eluant: ethyl acetate/heptane mixtures) to give the desired naphthol (yield: 536 mg, 2.65 mmol, 85%);

$v_{max}$/cm$^{-1}$ (neat) 3213br (OH stretch), 1734vs (C=O stretch), 1622s, 1588s, 1469vs, 1373s, 1298m, 1167s, 1101s, 832s;

$^1$H NMR (CDCl$_3$): $\delta_H$ 4.05 (s, 3H, CO$_2$CH$_3$), 7.16 (dd, J=5.8, 3.4 Hz, 1H, Ar-H), 7.40–7.48 (m, 3H, 3×Ar-H), 8.04 (dd, J=8.0, 1.2 Hz, 1H, 2-H), 8.25 (dd, J=7.4, 1.4 Hz, 1H, 7-H), 10.49 (s, 1H, OH); $^{13}$C NMR (CDCl$_3$) $\delta_C$ 53.8 (Me in CO$_2$Me), 115 6, 121.3, 122.2, 124.0, 125.2, 127.8, 132.3, 135.8, 153.2, 172.9 (C=O in CO$_2$Me);

m/z (C.I.) 203 [M+1].

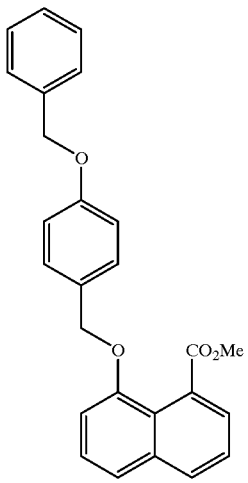

To a solution of 8-hydroxynaphthalene-1-methylcarboxylate (89 mg, 0.44 mmol) in dry DMF (4 mL) was added sodium hydride (11 mg, 0.48 mmol, 1.1 eq). The sodium hydride was added as 19 mg of a 60% dispersion in mineral oil that had been previously washed with 3×heptane portions under an inert atmosphere. The mixture was stirred for 30 minutes at room temperature and 4-benzyloxybenzyl chloride (113 mg, 0.48 mmol, 1.1 eq) was added. The resulting mixture was stirred at room temperature overnight. The reaction mixture was poured onto ice/water (100 mL), and the aqueous-DMF layer was extracted into ethyl acetate portions. The combined organic layers were washed (brine), dried (MgSO$_4$), filtered and concentrated in vacuo. The crude product was purified by column chromatography (silica gel, eluant:ethyl acetate/heptane mixtures) to give the desired ether (yield: 147 mg, 0.37 mmol, 84%);

$v_{max}$/cm$^{-1}$ (neat) 2948w, 1729vs (C=O in CO$_2$Me), 1612w, 1583w, 1514s, 1462m, 1374m, 1256vs, 1174m, 1051m;

$^1$H NMR (CDCl$_3$): $\delta_H$ 3.31 (s, 3H, CO$_2$CH$_3$), 5.09 (app d, J=8.0 Hz, 4H, 2×CH$_2$O), 6.96 (app d, J=7.6 Hz, 1H), 6.99–7.04 (m, 2H, 2×Ar-H), 7.31–7.48 (m, 2H, 2×Ar-H), 7.85 (dd, J=8.2, 1.0 Hz, 1H, naphthyl);

$^{13}$C NMR (CDCl$_3$) $\delta_C$ 51.9 (CO$_2$CH$_3$), 70.1 (CH$_2$O), 70.9 (CH$_2$O), 106.8, 115.0, 121.0, 121.4, 124.8, 125.4, 126.6, 127.5, 128.1, 128.5, 128.7, 129.5, 129.9, 130.4, 135.0, 135.9, 153.9, 158.9, 171.6 (C=O in CO$_2$Me);

m/z (ES$^+$) 436 [M+39, potassium adduct], 421 [M+23, sodium adduct].

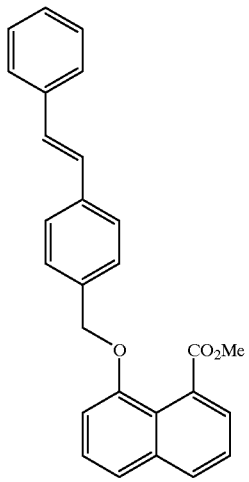

To a solution of 8-hydroxynaphthalene-1-methylcarboxylate (45 mg, 0.22 mmol) in dry DMF (4 mL) was added sodium hydride (6 mg, 0.24 mmol, 1.1 eq). The sodium hydride was added as 10 mg of a 60% dispersion in mineral oil that had been previously washed with 3×heptane portions under an inert atmosphere. The mixture was stirred for 30 minutes at room temperature and 4-chloromethylstilbene (56 mg, 0.24 mmol, 1.1 eq) was added. The resulting mixture was stirred at room temperature overnight. The reaction mixture was poured onto ice/water (100 mL) and the aqueous-DMF layer was extracted into ethyl acetate portions. The combined organic layers were washed (brine), dried (MgSO$_4$), filtered and concentrated in vacuo. The crude product was purified by column chromatography (silica gel, eluant:ethyl acetate/heptane mixtures) to give the desired ether (yield: 53 mg, 0.13 mmol, 61%);

$v_{max}$/cm$^{-1}$ (neat) 3027w, 1728vs (C=O in CO$_2$Me), 1619w, 1463m, 1374m, 1285m, 1257vs, 1201s, 1108m, 1051s;

$^1$H NMR (CDCl$_3$): $\delta_H$ 3.42 (s, 3H, CO$_2$CH$_3$), 5.18 (s, 2H, CH$_2$O), 6.97–6.98 (m, 1H, Ar-H), 7.09–7.18 (m, 2H, 2×vinyl), 7.27–7.29 (m, 1H, Ar-H), 7.35–7.59 (m, 12H, 12×Ar-H), 7.87 (dd, J=8.2, 1.4 Hz, 1H, naphthyl); $^{13}$C NMR (CDCl$_3$): $\delta_C$ 52.0 (Me in CO$_2$Me), 71.0, 106.9, 121.2, 121.5, 125.0, 125.4, 126.6, 126.7, 127.8, 128.2, 128.8, 129.0, 129.2, 129.5, 135.0, 135.4, 137.2, 137.5, 153.8, 171.7 (C=O in CO$_2$Me);

m/z (ES$^+$) 432 [M+39, potassium adduct], 417 [M+23, sodium adduct];

(ES$^-$) 394.

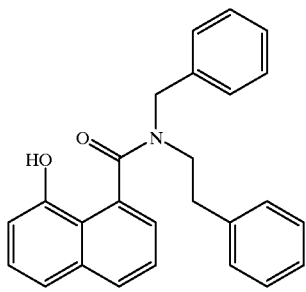

8-Hydroxy-naphthalene-1-carboxylic Acid Benzyl-phenethyl-amide 1,2-Dihydro-1-oxaacenaphthene-2-one (50 mg, 0.29 mmol) was suspended in dry methanol and stirred under an inert atmosphere. N-Benzylphenethylamine (373 mg, 0.37 mL, 1.76 mmol, 6 eq) in solution in methanol (4 mL) was added portionwise to the suspension. The resulting mixture was stirred at room temperature, 12 hours. The methanol was removed in vacuo, and the crude residue was purified by column chromatography (silica gel, eluant: ethyl acetate-heptane mixtures) to give the desired amide (yield: 32 mg, 0.08 mmol, 28%);

$v_{max}$/cm$^{-1}$ (neat) 3029br (OH stretch), 1602vs (C=O stretch in 3° amine), 1586vs, 1526s, 1496s;

$^1$H NMR (CDCl$_3$): $\delta_H$ 2.60 (quin, 1H), 3.00 (m, 1H), 3.21 (quin, 1H), 3.70 (m, 1H), 4.26 (q, 1H), 4.80 (q, 1H), 6.60–6.62 (m, 1H, Ar-H), 6.80–6.89 (m, 1H, Ar-H), 7.05–7.40 (m, 13H, 13×Ar-H), 7.74–7.83 (m, 1H, Ar-H); m/z (APCI) 382 [M+1].

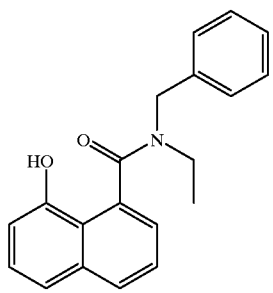

1,2-Dihydro-1-oxaacenaphthene-2-one (50 mg, 0.29 mmol) was suspended in dry methanol and stirred under an inert atmosphere. N-Ethylbenzylamine (238 mg, 1.76 mmol, 6 eq) in solution in methanol (4 mL) was added portionwise to the suspension. The resulting mixture was stirred at room temperature, 12 hours. The methanol was removed in vacuo, and the crude residue was purified by column chromatography (silica gel, eluant:ethyl acetate-heptane mixtures) to give the desired amide (yield: 27 mg, 0.09 mmol, 31%);

$v_{max}$/cm$^{-1}$ (neat) 3924br (OH stretch), 1607vs (C=O stretch in 3° amine), 1581s, 1526m, 1477m;

$^1$H NMR (CDCl$_3$): $\delta_H$ 0.95 and 1.16 (t, J=7.1 Hz, 3H (2 signals), CH$_3$), 3.12 (m, 1H), 3.50 (m, 1H), 4.36 (m, 1H), 4.82 (q, 1H), 6.88–6.90 (m, 1H, Ar-H), 7.14–7.43 (m, 10H, 10×Ar-H), 7.75–7.84 (m, 1H, Ar-H);

m/z (APCI) 306 [M+1].

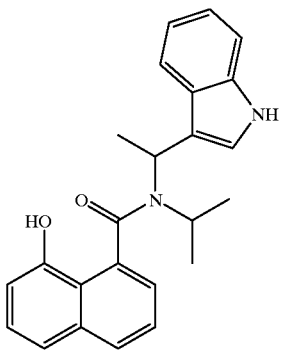

1,2-Dihydro-1-oxaacenaphthene-2-one (50 mg, 0.29 mmol) was suspended in dry methanol and stirred under an inert atmosphere. N-[(Methyl,3'-indoyl)methyl]-isopropylamine (357 mg, 1.76 mmol, 6 eq) in solution in methanol (4 mL) was added portionwise to the suspension. The resulting mixture was stirred at room temperature, 12 hours. The methanol was removed in vacuo, and the crude residue was purified by column chromatography (silica gel, eluant:ethyl acetate/heptane mixtures) to give the desired amide (yield: 36 mg, 0.10 mmol, 35%);

$v_{max}$/cm$^{-1}$ (neat) 3306br (OH stretch), 1624vs (C=O stretch in 3° amine);

$^1$H NMR (CDCl$_3$): $\delta_H$ 1.31 (d, J=6.8 Hz, 6H, 2×Me in $^i$Pr group), 1.78 (d, J=6.8 Hz, 3H, Me), 4.38 (m, 1H, CHMe$_2$), 5.05 (m, 1H, CHMe), 6.25 (m, 1H, ArH), 6.76–6.77 (m, 1H, ArH), 7.01–7.05 (m, 2H, 2×ArH), 7.15–7.16 (m, 1H, ArH), 7.30–7.38 (m, 4H, 4×ArH), 7.49–7.51 (m, 1H, ArH), 7.99 (br s, 1H, NH), 8.31 (d, 1H, ArH);

m/z (APCI) 373 [M+1];

(ES$^-$) 371 [M-1].

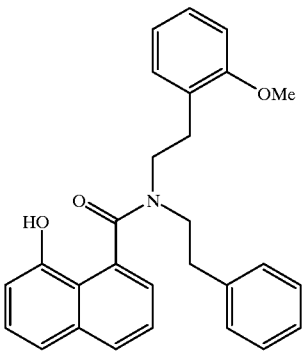

1,2-Dihydro-1-oxaacenaphthene-2-one (50 mg, 0.29 mmol) was suspended in dry methanol and the reaction mixture stirred under an inert atmosphere. N-[Ethyl-2-(2'-methoxy)phenyl]phenethylamine (450 mg, 1.76 mmol, 6 eq) in solution in methanol (4 mL) was added portionwise to the suspension. The resulting mixture was stirred at room temperature, 12 hours. The methanol was removed in vacuo and the crude residue was purified by column chromatography (silica gel, eluant:ethyl acetate/heptane mixtures) to give the desired amide (yield: 32 mg, 0.08 mmol, 26%);

$v_{max}$/cm$^{-1}$ (neat) 3056br (OH stretch), 1602vs (C=O stretch in 3° amine);

$^1$H NMR (CDCl$_3$): $\delta_H$ 2.55–2.65 (m, 2H, 2×aliphatic), 2.95–3.05 (m, 1H, aliphatic), 3.05–3.15 (m, 3H, 3×aliphatic), 3.75–3.79 (m, 2H, 2×aliphatic), 3.75 and 3.79 (2xs, 3H, OMe (2 signals)), 6.15 (m, 1H, ArH), 6.25 (m, 1H, ArH), 6.69–6.71 (m, 2H, 2×ArH), 6.83–6.85 (m, 2H, 2×ArH), 7.02–7.04 (m, 2H, 2×ArH), 7.05–7.34 (m, 6H, 6×ArH), 7.75–7.76 (m, 1H, ArH);

m/z (APCI) 426 [M+1], 256.

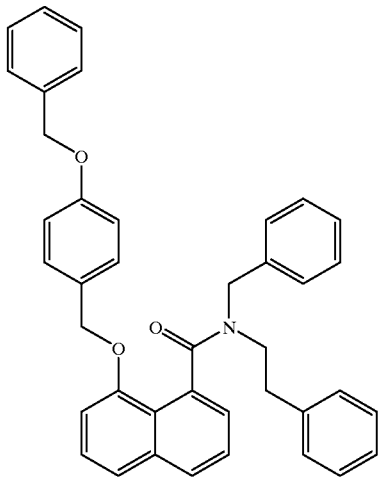

8-(4-Benzyloxy-benzyloxy)-naphthalene-1-carboxylic Acid Benzyl-phenethyl-amide

To a solution of the substituted naphthol (32 mg, 0.08 mmol) in dry DMF (2 mL) was added sodium hydride (2 mg, 0.09 mmol, 1.1 eq). The sodium hydride was added as 4 mg of a 60% dispersion in mineral oil that had been previously washed with 3×heptane portions under an inert atmosphere. The mixture was stirred for 30 minutes at room temperature, and 4-benzyloxybenzyl chloride (21 mg, 0.09 mmol, 1.1 eq) was added. The resulting mixture was stirred at room temperature overnight. The reaction mixture was poured onto ice/water (100 mL), and the aqueous-DMF layer was extracted into ethyl acetate portions. The combined organic layers were washed (brine), dried ($MgSO_4$), filtered and concentrated in vacuo. The crude product was purified by column chromatography (silica gel, eluant:ethyl acetate/heptane mixtures) to give the desired ether (yield: 27 mg, 0.05 mmol, 58%);

$v_{max}/cm^{-1}$ (neat) 3029w, 2930w, 1636vs (C=O in 3° amide), 1583w, 1513s, 1467m, 1373m, 1244vs, 1175m, 1026m, 823s;

$^1$H NMR ($CDCl_3$): $\delta_H$ 2.40–5.20 (m, 10H, 10×aliphatic), 6.46 (m, 1H, Ar-H), 6.90–7.47 (m, 23H, 23×Ar-H), 7.81 (t, 1H, naphthyl);

$^{13}$C NMR ($CDCl_3$): $\delta_C$ 33.4 and 34.6 ($CH_2$), 46.1 and 47.7 ($CH_2Ar$), 50.9 and 53.5 ($CH_2Ar$), 69.9 and 70.2 ($CH_2O$), 70.6 and 70.9 ($CH_2O$), 106.8 and 107.2, 114.9 and 115.0, 121.2 and 121.3, 121.7, 122.0, 124.8 and 124.9, 125.8 and 125.9, 126.1 and 126.2, 126.5, 127.3, 127.4 and 127.5, 127.6, 128.0 and 128.1, 128.2, 128.4 and 128.5, 128.5 and 128.6, 128.7 and 128.8, 130.1 and 130.3, 132.8 and 133.0, 135.3 and 135.4, 136.9 and 137.0, 138.3 and 138.6, 139.6, 154.4 and 154.6, 158.9 and 159.0, 172.8 (C=O in amide);

m/z ($ES^+$) 616 [M+39, potassium adduct], 600 [M+23, sodium adduct].

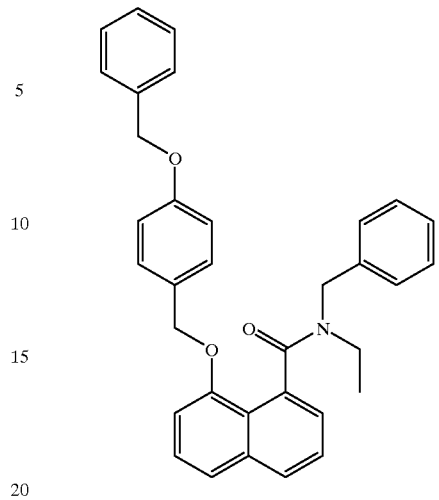

8-(4-Benzyloxy-benyloxy)-naphthalene-1-carboxylic Acid Benzyl-ethyl-amide

To a solution of the substituted naphthol (27 mg, 0.09 mmol) in dry DMF (2 mL) was added sodium hydride (2 mg, 0.09 mmol, 1.1 eq). The sodium hydride was added as 4 mg of a 60% dispersion in mineral oil that had been previously washed with 3×heptane portions under an inert atmosphere. The mixture was stirred for 30 minutes at room temperature and 4-benzyloxybenzyl chloride (23 mg, 0.10 mmol, 1.1 eq) was added. The resulting mixture was stirred at room temperature overnight. The reaction mixture was poured onto ice/water (100 mL), and the aqueous-DMF layer was extracted into ethyl acetate portions. The combined organic layers were washed (brine), dried ($MgSO_4$), filtered and concentrated in vacuo. The crude product was purified by column chromatography (silica gel, eluant:ethyl acetate/heptane mixtures) to give the desired ether (yield: 18 mg, 0.04 mmol, 40%);

$v_{max}/cm^{-1}$ (neat) 2931w, 1630vs (C=O in 3° amide), 1583w, 1454m, 1375m, 1242vs, 1175m, 1050m, 824s;

$^1$H NMR ($CDCl_3$): $\delta_H$ 3.00 (q, 1H), 3.20 (double sextet, 1H), 3.45 (m, 0.5H), 4.20 (q, 2×0.5H), 4.60 (s, 1H), 4.85–4.98 (m, 2×0.5H), 5.00–5.10 (m, 1.5H), 5.20 (q, 1H), 6.90–7.05 (m, 4H, 4×Ar-H), 7.21–7.47 (m, 15H, 15×Ar-H), 7.78–7.82 (m, 1H, Ar-H), $^{13}$C NMR ($CDCl_3$) $\delta_C$ 12.3 and 12.9 (Me, 2 signals), 38.8, 43.2, 46.5, 52.4, 65.1, 70.1 and 70.6 ($CH_2Ar$, 2 signals), 106.6, 107.3, 114.9, 115.0, 121.1, 121.2, 124.6, 124.9, 125.8, 126.5, 127.0, 127.4, 127.5, 127.8, 128.0, 128.2, 128.4, 128.5, 128.6, 128.8, 129.0, 129.6, 130.3, 133.1, 135.4, 137.0, 138.5, 154.5, 158.9, 172.6 (C=O in amide);

m/z ($ES^+$) 540 [M+39, potassium adduct], 524 [M+23, sodium adduct].

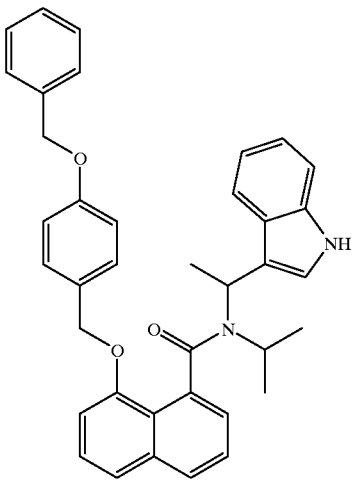

8-(4-Benzyloxy-benzyloxy)-naphthalene-1-carboxylic Acid [1-(1H-indol-3-yl)-ethyl]-isopropyl-amide To a solution of the substituted naphthol (36 mg, 0.10 mmol) in dry DMF (4 mL) was added sodium hydride (5 mg, 0.21 mmol, 2.1 eq). The sodium hydride was added as 8 mg of a 60% dispersion in mineral oil that had been previously washed with 3×heptane portions under an inert atmosphere. The mixture was stirred for 30 minutes at room temperature, and 4-benzyloxybenzyl chloride (26 mg, 0.11 mmol, 1.1 eq) was added. The resulting mixture was stirred at room temperature overnight. The reaction mixture was poured onto ice/water (100 mL), and the aqueous-DMF layer was extracted into ethyl acetate portions. The combined organic layers were washed (brine), dried (MgSO$_4$), filtered and concentrated in vacuo. The crude product was purified by column chromatography (silica gel, eluant:ethyl acetate/heptane mixtures) to give the desired ether (yield: 15 mg, 0.03 mmol, 26%);

$v_{max}$/cm$^{-1}$ (neat) 2969m, 1694w, 1642m (C=O in 3° amide), 1612s, 1585w, 1512vs, 1465s, 1367m, 1242vs, 1175s;

$^1$H NMR (CDCl$_3$): $\delta_H$ 1.27 (d, J=7.2 Hz, 6H, 2×Me in $^i$Pr group), 1.75 (d, J=7.2 Hz, 3H, Me), 3.90 (m, 1H, CHMe$_2$), 4.10 (m, 1H, CHMe), 5.02–5.11 (m, 4H, 2×CH$_2$O), 6.88–8.20 (m, 20H, 20×ArH).

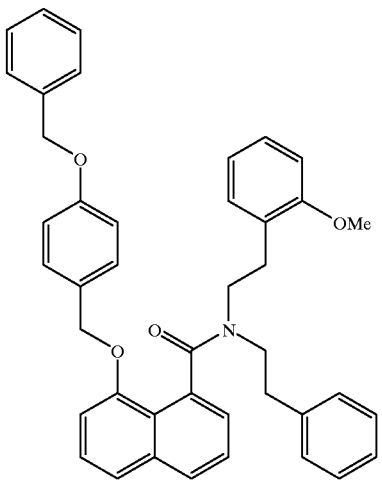

8-(4-Benzyloxy-benzyloxy)-naphthalene-1-carboxylic Acid [2-(2-methoxy-phenyl)-ethyl]-phenethyl-amide To a solution of the substituted naphthol (32 mg, 0.08 mmol) in dry DMF (4 mL) was added sodium hydride (2 mg, 0.09 mmol, 1.1 eq). The sodium hydride was added as 4 mg of a 60% dispersion in mineral oil that had been previously washed with 3×heptane portions under an inert atmosphere. The mixture was stirred for 30 minutes at room temperature, and 4-benzyloxybenzyl chloride (21 mg, 0.09 mmol, 1.1 eq) was added. The resulting mixture was stirred at room temperature overnight. The reaction mixture was poured onto ice/water (100 mL) and the aqueous-DMF layer was extracted into ethyl acetate portions. The combined organic layers were washed (brine), dried (MgSO$_4$), filtered and concentrated in vacuo. The crude product was purified by column chromatography (silica gel, eluant: ethyl acetate-heptane mixtures) to give the desired ether (yield: 25 mg, 0.04 mmol, 50%);

$v_{max}$/cm$^{-1}$ (neat) 3030w, 2935w, 2867w, 1635vs, (C=O in 3° amide), 1584s, 1514vs, 1492m, 1467s, 1259vs, 1175m;

$^1$H NMR (CDCl$_3$): $\delta_H$ 2.58–2.53 (m, 2H, CH$_2$), 2.68–2.88 (m, 2H, CH$_2$), 2.90–3.10 (m, 2H, CH$_2$), 3.10–3.20 and 3.58–3.62 (2×m, 2H (2 signals), CH$_2$), 3.58 and 3.78 (2×s, 3H (2 signals), OCH$_3$), 4.90 (q, 1H), 5.20 (q, 1H), 6.59–6.82 (m, 3H), 6.90–7.02 (m, 4H), 7.05–7.15 (m, 2H), 7.15–7.30 (m, 5H), 7.30–7.43 (m, 9H), 7.82 (m, 1H);

$^{13}$C NMR (CDCl$_3$) $\delta_C$ 33.9, 34.0, 34.9, 35.0, 46.6, 46.7, 51.6, 55.3, 65.1, 69.9, 70.1, 70.7, 106.8, 111.7, 112.0, 113.8, 114.6, 114.7, 114.9, 120.9, 121.9, 124.8, 124.9, 125.8, 126.3, 126.5, 127.5, 128.0, 128.5, 128.6, 128.9, 129.4, 130.2, 130.3, 133.1, 135.3, 137.1, 138.5, 139.7, 140.1, 141.3, 154.5, 158.9, 159.6, 159.8, 172.4 (C=O in amide);

m/z (ES$^+$) 660 [M+39, potassium adduct], 644 [M+23, sodium adduct].

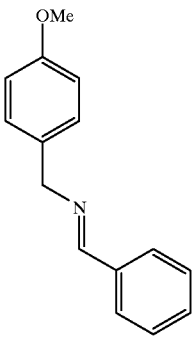

4-Methoxybenzylamine (500 mg, 3.64 mmol, 0.48 mL) and benzaldehyde (387 mg, 0.37 mL, 3.64 mmol, 1 eq) were combined in solution in dichloromethane containing molecular sieves (previously activated by oven drying overnight) and the resulting mixture stirred at room temperature overnight. The reaction was followed by i.r. spectroscopy. The molecular sieves were removed by filtration, and the solvent was removed in vacuo. The imine was clean enough (by $^1$H nmr, i.r. and mass spectroscopy) to be used in the next stage without further purification; $v_{max}$/cm$^{-1}$ (neat) 1644s (C=N stretch in imine), 1611m, 1580w, 1513vs, 1247vs;

$^1$H NMR (CDCl$_3$): $\delta_H$ 3.77 (s, 3H, OCH$_3$), 4.75 (s, 2H, CH$_2$), 6.86–6.92 (m, 2H, part of AA'BB' system), 7.23–7.25 (m, 2H, part of AA'BB' system), 7.38–7.40 (m, 3H), 7.75–7.77 (m, 2H), 8.34 (s, 1H, imine);

m/z (ES$^+$) 226 [M+1].

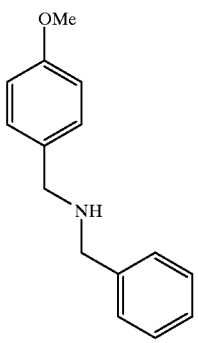

The imine (820 mg, 3.64 mmol) was dissolved in absolute ethanol (25 mL) and treated with sodium borohydride (207 mg, 5.47 mmol, 1.5 eq) and left to stir at room temperature overnight. The ethanol was removed in vacuo, and the residue was quenched with water. The aqueous layer was then extracted into ethyl acetate portions which were combined, washed (brine), dried (MgSO$_4$), filtered and concentrated in vacuo. The crude product was purified by column chromatography (silica gel, eluant: 25%; 50%; 75% ethyl acetate/heptane mixtures) to give the desired secondary amine (yield: 731 mg, 3.22 mmol, 88%);

$v_{max}$/cm$^{-1}$ (neat) 3334br (NH stretch), 1611s, 1585m, 1557m, 1512vs, 1454s, 1361w, 1301m, 1246vs;

$^1$H NMR (CDCl$_3$): $\delta_H$ 1.69 (br s, 1H, NH), 3.73 (s, 2H, CH$_2$), 3.78 (app s, 5H, OCH$_3$ and CH$_2$), 6.85–6.87 (m, 2H, part of AA'BB' system), 7.23–7.24 (m, 2H, part of AA'BB' system), 7.31–7.33 (m, 5H, mono-substituted ring);

$^{13}$C NMR (CDCl$_3$): $\delta_C$ 52.7 (CH$_2$N), 53.2 (CH$_2$N), 55.4 (OMe), 113.9, 127.0, 128.3, 128.5, 129.5, 132.6, 140.5, 158.8;

m/z (ES$^+$) 228 [M+1].

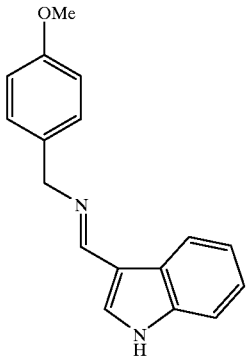

4-Methoxybenzylamine (500 mg, 3.64 mmol, 0.48 mL) and indole-3-carboxaldehyde (529 mg, 3.64 mmol, 1 eq) were combined in solution in dichloromethane containing molecular sieves (previously activated by oven drying overnight) and the resulting mixture stirred at room temperature overnight. The reaction was followed by i.r. spectroscopy. The molecular sieves were removed by filtration, and the solvent was removed in vacuo. The imine was clean enough (by $^1$H nmr, i.r. and mass spectroscopy) to be used in the next stage without further purification;

$v_{max}$/cm$^{-1}$ (neat) 1633s (C=N stretch in imine), 1510vs, 1441m, 1246vs, 1031s;

$^1$H NMR (CDCl$_3$): $\delta_H$ 3.49 (s, 1H), 3.81 (s, 3H, OCH$_3$), 4.78 (s, 2H, CH$_2$), 6.88–6.94 (m, 2H, part of AA'BB' system), 7.20–7.24 (m, 2H, part of AA'BB' system), 7.31–7.42 (m, 2H), 7.52 (m, 1H), 8.31–8.36 (m, 1H), 8.58 (s, 1H);

m/z (ES$^+$) 265 [M+1].

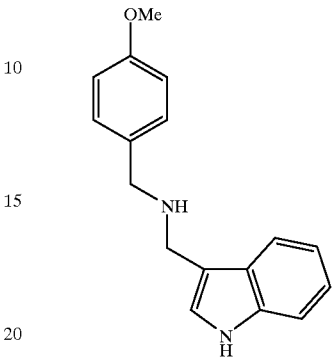

The imine (962 mg, 3.64 mmol) was dissolved in absolute ethanol (30 mL) and treated with sodium borohydride (207 mg, 5.47 mmol, 1.5 eq) and left to stir at room temperature overnight. The ethanol was removed in vacuo, and the residue was quenched with water. The aqueous layer was then extracted into ethyl acetate portions which were combined, washed (brine), dried (MgSO$_4$), filtered and concentrated in vacuo. The crude product was purified by column chromatography (silica gel, eluant: 25%; 50%; 75% ethyl acetate/heptane mixtures) to give the desired secondary amine (yield: 101 mg, 0.37 mmol, 11%);

$v_{max}$/cm$^{-1}$ (neat) 3407br (NH stretch), 1611m, 1513s, 1455s, 1339m, 1302m, 1247s, 1176s, 1033s, 934vs;

$^1$H NMR (CDCl$_3$): $\delta_H$ 1.80 (br s, 1H, NH-aliphatic), 3.80 (s, 3H, OCH$_3$), 3.82 (s, 2H, CH$_2$), 3.99 (s, 2H, CH$_2$), 6.86–6.88 (m, 3H), 7.07–7.13 (m, 2H), 7.19 (t, J=7.6 Hz, 1H), 7.24–7.28 (m, 2H, part of AA'BB' system), 7.33 (d, J=8.0 Hz, 1H), 7.63 (d, J=7.6 Hz, 1H), 8.26 (br s, 1H, NH-indole);

$^{13}$C NMR (CDCl$_3$): $\delta_C$ 49.2 (OMe), 55.4 (CH$_2$N), 57.5 (CH$_2$N), 111.0, 113.8, 114.1, 119.3, 120.1, 122.0, 123.6, 128.0, 130.3, 130.8, 132.4, 136.5, 158.5, 171.4;

m/z (ES$^+$) 228 [M+1].

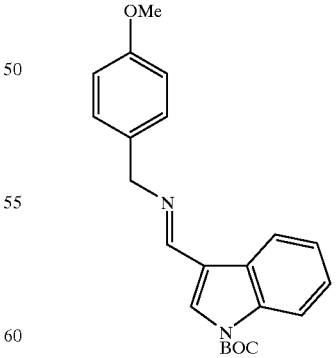

4-Methoxybenzylamine (666 mg, 4.85 mmol, 0.63 mL) and N-BOC-indole-3-carboxaldehyde (1.19 g, 4.85 mmol, 1 eq) were combined in solution in dichloromethane containing molecular sieves (previously activated by oven drying overnight) and the resulting mixture stirred at room temperature overnight. The reaction was followed by i.r. spectroscopy. The molecular sieves were removed by filtration, and the solvent was removed in vacuo. The imine was clean enough (by $^1$H nmr, i.r. and mass spectroscopy) to be used in the next stage without further purification;

$v_{max}$/cm$^{-1}$ (neat) 1738vs (C=O stretch in BOC group), 1644vs (C=N stretch in imine);

$^1$H NMR (CDCl$_3$): $\delta_H$ 1.68 (s, 9H, $^t$Bu in BOC group), 3.80 (s, 3H, OCH$_3$), 4.78 (s, 2H, CH$_2$), 5.29 (s, 1H, imine), 6.88–6.92 (m, 2H, part of AA'BB' system), 7.28–7.34, (m, 2H, part of AA'BB' system), 7.34–7.38 (m, 1H), 7.87 (s, 1H), 8.14 (d, J=8.4 Hz, 1H), 8.39 (d, J=7.6 Hz, 1H), 8.53 (s, 1H, NH-indole);

m/z (ES$^+$) 365 [M+1].

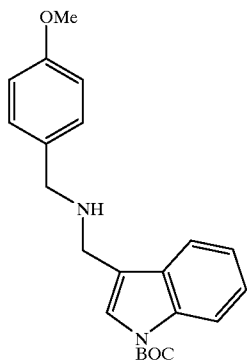

The imine (1.16 g, 3.18 mmol) was dissolved in absolute ethanol (25 mL) and treated with sodium borohydride (120 mg, 3.18 mmol, 1 eq) and left to stir at room temperature overnight. The ethanol was removed in vacuo, and the residue was quenched with water. The aqueous layer was then extracted into ethyl acetate portions which were combined, washed (brine), dried (MgSO$_4$), filtered and concentrated in vacuo. The crude product was purified by column chromatography (silica gel, eluant: 25%; 50%; 75% ethyl acetate/heptane mixtures) to give the desired secondary amine (yield: 1.10 g, 3.01 mmol, 95%);

$v_{max}$/cm$^{-1}$ (neat) 3328w, 2978m, 2933m, 2834m, 1732vs (C=O in BOC group), 1612s, 1513s, 1452vs, 1378vs, 1249s, 1159s;

$^1$H NMR (CDCl$_3$): $\delta_H$ 1.66 (s, 9H, $^t$Bu in BOC group), 3.79 (s, 3H, OCH$_3$), 3.81 (2H, CH$_2$N), 3.91 (2H, CH$_2$N), 6.85–6.89 (m, 2H, part of AA'BB' system), 7.21–7.33 (m, 4H), 7.52 (s, 1H), 7.58 (d, J=7.6 Hz, 1H), 8.14 (d, J=7.2 Hz, 1H);

$^{13}$C NMR (CDCl$_3$) $\delta_C$ 28.3, 43.9, 53.0, 55.3, 83.5, 113.9, 115.4, 119.4, 119.7, 120.6, 123.6, 124.5, 129.4, 129.5, 130.2, 132.5, 149.9, 158.8 (C=O in BOC); m/z (ES$^+$) 405 [M+39, potassium adduct], 389 [M+23, sodium adduct], 367 [M+1].

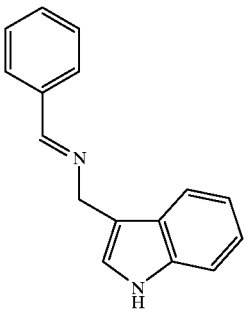

Tryptamine (500 mg, 3.12 mmol) and benzaldehyde (331 mg, 0.32 mL, 3.12 mmol, 1 eq) were combined in solution in dichloromethane (20 mL) containing molecular sieves (previously activated by oven drying overnight) and the resulting mixture stirred at room temperature overnight. The reaction was followed by i.r. spectroscopy. The molecular sieves were removed by filtration, and the solvent was removed in vacuo. The imine was clean enough (by $^1$H nmr, i.r. and mass spectroscopy) to be used in the next stage without further purification;

$v_{max}$/cm$^{-1}$ (neat) 1645s (C=N stretch in imine);

$^1$H NMR (CDCl$_3$): $\delta_H$ 3.18 (t, J=7.4 Hz, 2H, CH$_2$-indole), 3.95 (t, J=7.2 Hz, 2H, CH$_2$-indole), 7.03 (d, J=1.6 Hz, 1H), 7.13 (t, J=7.2 Hz, 1H), 7.20 (t, J=7.4 Hz, 1H), 7.35–7.42 (m, 4H), 7.67–7.73 (m, 3H), 7.96 (br s, 1H, NH-indole), 8.18 (s, 1H, imine);

m/z (APCI) positive scan: 249 [M+1]; negative scan: 247 [M−1].

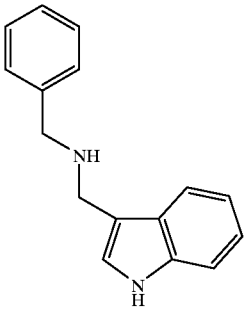

The imine (774 mg, 3.12 mmol) was dissolved in absolute ethanol (30 mL) and treated with sodium borohydride (177 mg, 4.68 mmol, 1.5 eq) and left to stir at room temperature overnight. The ethanol was removed in vacuo, and the residue was quenched with water. The aqueous layer was then extracted into ethyl acetate portions which were combined, washed (brine), dried (MgSO$_4$), filtered and concentrated in vacuo. The crude product was purified by column chromatography (silica gel, eluant: 25%; 50%; 75% ethyl acetate/heptane mixtures) to give the desired secondary amine (yield: 680 mg, 2.72 mmol, 87%);

$v_{max}$/cm$^{-1}$ (neat) 3419s (NH stretch), 2920m, 2807m, 1587w, 1494w, 1455s, 1342m, 1226w, 1094m, 747vs;

$^1$H NMR (CDCl$_3$): $\delta_H$ 1.99 (s, 1H, NH-aliphatic), 2.99 (s, 4H, 2×CH$_2$), 3.80 (s, 2H, CH$_2$), 6.94 (d, J=1.6 Hz, 1H, Ar-H), 7.08–7.11 (m, 1H, Ar-H), 7.15–7.20 (m, 1H, Ar-H), 7.20–7.31 (m, 5H, 5×Ar-H), 7.59 (d, J=8 Hz, 1H, Ar-H), 8.23 (br s, 1H, NH-indole);

$^{13}$C NMR (CDCl$_3$) $\delta_C$ 25.8 (CH$_2$), 49.4 (CH$_2$), 53.9 (CH$_2$), 111.3, 113.8, 118.9, 119.3, 122.1, 127.1, 127.5, 128.3, 128.5, 136.5, 140.1;

m/z (ES$^+$) 251 [M+1].

Further examples of dendroids are given in Table 1 below.

A further embodiment of the invention is the group X. This functional group is separately attached to the core monomer A or indeed to any other suitable moiety in a synthetically useful manner for "combinatorial library chemistry". Those skilled in the art will readily appreciate that such dendroids can be produced as mixtures of large numbers of compounds when, for example $X=(CH_2)_nCO_2H$ and is attached to a suitable resin for solid phase synthesis, such as by ester linkage to Wang resin (Hobbs-Dewitt S., Molecular Diversity Strategies, *Pharmaceutical News*, 1994; 1:11–14).

Hence, the novel dendroids in this patent may be useful to treat a wide range of diseases that may include cancer (targets: e.g., Ras farnesylation, Ras/Raf complex, Rb and p-53 proteins), Alzheimer's disease (target: e.g., β-amyloid protein) and thrombosis (target: Fibrinogen), inflammatory diseases (target: cytokines), bacterial resistance (target: glycopeptides). Drugs composed of such low molecular weights may be given by oral, rectal, IV, IM, IP, aerosol, skinpatch, or nasal delivery.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 200 mg preferably 0.5 mg to 100 mg according to the particular application and the potency of the active component. The composition can, if desired, also contain other compatible therapeutic agents.

In therapeutic use the compounds utilized in the pharmaceutical method of this invention are administered at the initial dosage of about 0.01 mg to about 500 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Examples of dendroids are illustrated by the following which are not meant to limit the scope of the instant invention.

TABLE 1
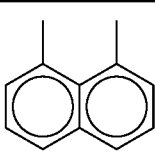
| No. | A | B | C | D | E | F | G |
|---|---|---|---|---|---|---|---|
| 1 |  |  | CH$_2$CON< | — | CONH$_2$ | H | H |
| 2 | 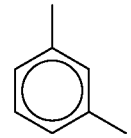 | O— |  | — | CH$_2$-3-indole | — | — |
| 3 | 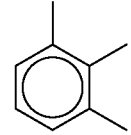 | CH$_2$O— | O— | CH$_2$O— | CH$_2$-2-imidazole | — | — |
| 4 | 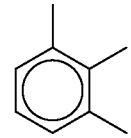 | O— | (CH$_2$)$_2$— | NHCO— | CH$_2$Ph | — | — |
| 5 | 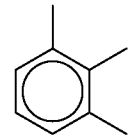 | O— |  | (CH$_2$)$_2$— | CH$_2$Ph(4-OH) | — | — |
| 6 |  | CO— | 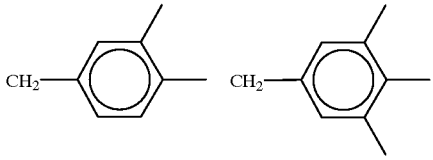 | 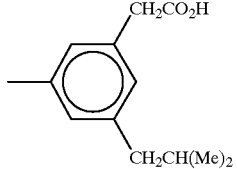 | CH$_3$ | H | Ph |
| No. | H | I | J | K | L | M |
|---|---|---|---|---|---|---|
| 1 | (CH$_2$)$_2$SMe | (CH$_2$)$_3$NHC(=NH)NH$_2$ | — | bond | — | — |
| 2 | CH$_2$CO$_2$H <br> (with 3,5-disubstituted phenyl: CH$_2$CH(Me)$_2$) | H | H | — | — | — |

TABLE 1-continued

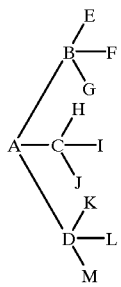

| | | | | | | |
|---|---|---|---|---|---|---|
| 3 | $CH_2CO_2H$ | — | — | $(CH_2)_2SH$ | — | — |
| 4 | $CH(Me)_2$ | — | — | $(CH_2)_4NH_2$ | — | — |
| 5 | $(CH_2)_2CONH_2$ | $CH_2CO_2H$ | — | $CH_2OH$ | — | — |
| 6 | $OCH_2CO_2H$ | $OCH_2CONH_2$ | — | $N(Me)(CH_2)_2NMe_2$ | $(CH_2)_2OH$ | $OCH_2CO_2H$ |

What is claimed is:

1. A compound of formula

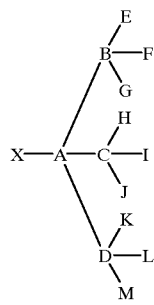

or a pharmaceutically acceptable salt thereof wherein:
  A is selected from [1,2,3,5-tetrasubstituted or 1,2,4- or 1,3,5-trisubstituted benzene; 2,3,4,5-tetrasubstituted or 2,3,5; or 2,4,5-trisubstituted thiophenes; 2,3,4,6- or 2,4,5,6-tetrasubstituted or 2,3,5-; or 2,3,6-trisubstituted pyridine;] 1,8,X-trisubstituted naphthalene, ortho-, meta-, or perisubstituted naphthalene;
  B, C, and D are covalently bonded to A and are the same or different and are independently selected from —Y—Z— below;
  Y is selected from =$(CH_2)_n$—O—, O—$(CH_2)_n$—, —NHCO$(CH_2)_n$, $(CH_2)_n$NHCO—, CONH-$(CH_2)_n$, $(CH_2)_n$CONH; —$(CH_2)_n$—, or a bond wherein n is an integer of from 0 to 3.
  Z is di, tri, or tetrasubstituted benzene as defined above or is selected from A above, or is a substituted amine or amide selected from —$CH_2$-3-indole and —$CH_2$-2-imidazole or a carbamate, or a bond;
  E, F, G, H, I, J, K, L, and M are each independently selected from B, C, and D above; X is hydrogen, $(CH_2)_nCO_2R$ wherein R is an ester; N or a function group attached to the one monomer A above.

2. A pharmaceutical composition comprising a therapeutically effective amount of a compound according to claim 1 together with a pharmaceutically acceptable carrier.

3. A method for the treatment of bacterial infections comprising administering to a mammal in need of said treatment a therapeutically effective amount of a compound of claim 1.

4. A compound according to claim 1 and selected from:
  8-(4-Bromo-benzyloxy)-naphthalene-1-carboxylic acid dimethylamide;
  8-(4-Methoxy-benzyloxy)-naphthalene-1-carboxylic acid dimethylamide;
  8-(3,4-Dimethoxy-benzyloxy)-naphthalene-1-carboxylic acid dimethylamide;
  8-(3,4,5-Trimethoxy-benzyloxy)-naphthalene-1-carboxylic acid dimethylamide;
  8-(3,5-Dimethoxy-benzyloxy)-naphthalene-1-carboxylic acid dimethylamide;
  8-(Biphenyl-4-ylmethoxy)-naphthalene-1-carboxylic acid dimethylamide;
  8-(4-Benzyloxy-benzyloxy)-naphthalene-1-carboxylic acid dimethylamide;
  8-(4-Styryl-benzyloxy)-naphthalene-1-carboxylic acid dimethylamide;
  8-Hydroxy-naphthalene-1-carboxylic acid benzyl-phenethyl-amide;
  8-(4-Benxyloxy-benzyloxy)-naphthalene-1-carboxylic acid benzyl-phenethyl-amide;
  8-(4-Benxyloxy-benzyloxy)-naphthalene-1-carboxylic acid benzyl-ethyl-amide;
  8-(4-Benxyloxy-benzyloxy)-naphthalene-1-carboxylic acid [1-(1H-indol-3-yl)-ethyl]-isoproyl-amide; and
  8-(4-Benxyloxy-benzyloxy)-naphthalene-1-carboxylic acid [2-(2-methoxy-phenyl)-ethyl]-phenethyl-amide.

* * * * *